United States Patent
Dioum et al.

(10) Patent No.: US 12,350,287 B2
(45) Date of Patent: Jul. 8, 2025

(54) METHOD OF REDUCING AGE-RELATED SYSTEMIC CHRONIC INFLAMMATION

(71) Applicant: The Quaker Oats Company, Chicago, IL (US)

(72) Inventors: El Hadji M. Dioum, Chicago, IL (US); YiFang Chu, Glenview, IL (US)

(73) Assignee: The Quaker Oats Company, Chicago, IL (US)

( * ) Notice: Subject to any disclaimer, the term of this patent is extended or adjusted under 35 U.S.C. 154(b) by 531 days.

(21) Appl. No.: 17/876,268

(22) Filed: Jul. 28, 2022

(65) Prior Publication Data

US 2023/0038754 A1 Feb. 9, 2023

Related U.S. Application Data

(60) Provisional application No. 63/226,553, filed on Jul. 28, 2021.

(51) Int. Cl.
| | | |
|---|---|---|
| *A61K 31/716* | (2006.01) | |
| *A61K 9/00* | (2006.01) | |
| *A61K 31/192* | (2006.01) | |
| *A61P 29/00* | (2006.01) | |

(52) U.S. Cl.
CPC .......... *A61K 31/716* (2013.01); *A61K 9/0053* (2013.01); *A61K 31/192* (2013.01); *A61P 29/00* (2018.01)

(58) Field of Classification Search
None
See application file for complete search history.

(56) References Cited

U.S. PATENT DOCUMENTS

| | | |
|---|---|---|
| 8,241,696 B2 | 8/2012 | Chung et al. |
| 8,574,644 B2 | 11/2013 | Chatel et al. |
| 8,586,113 B2 | 11/2013 | Carder et al. |
| 8,591,970 B2 | 11/2013 | Chatel et al. |
| 8,795,754 B2 | 8/2014 | Chatel et al. |
| 8,802,177 B2 | 8/2014 | Chatel et al. |
| 9,011,947 B2 | 4/2015 | Carder et al. |
| 9,149,060 B2 | 10/2015 | Chatel et al. |
| 9,504,272 B2 | 11/2016 | Carder et al. |
| 9,510,614 B2 | 12/2016 | Carder et al. |
| 9,622,500 B2 | 4/2017 | Carder et al. |
| 10,092,016 B2 | 10/2018 | Avila et al. |
| 2013/0183405 A1 | 7/2013 | Chatel et al. |
| 2016/0081375 A1 | 3/2016 | Chatel et al. |
| 2016/0198754 A1 | 7/2016 | Carder et al. |
| 2017/0265503 A1 | 9/2017 | Chung et al. |
| 2017/0273337 A1 | 9/2017 | Brijwani et al. |

FOREIGN PATENT DOCUMENTS

| | | | |
|---|---|---|---|
| CN | 101991163 | * | 8/2009 |
| WO | 2019/165145 | | 8/2019 |

OTHER PUBLICATIONS

Communication Pursuant to Rule 114(2) EPC—Observations by Third Party issued in EP Appl. No. 22757754.1 on Aug. 9, 2024.
Key Attributes of TKDL—Hartmaan 1926 AD—Mohammad Najmul Ghani Khan pp. 1033-1034 (3 pages).
Alpert et al., "A Clinically Meaningful Metric of Immune Age Derived from High-Dimensional Longitudinal Monitoring," Nature Medicine, vol. 25, Mar. 2019, pp. 487-495.
Goronzy et al., "Understanding immunosenescence to improve responses to vaccines," Nat. Immunol. 14, 428-436 (2013).
Deleidi et al., "Immune ageing, dysmetabolism and inflammation in neurological diseases," Front. Neurosci. 9, 172 (2015).
Dorshkind et al., "The ageing immune system: is it ever too old to become young again?," Nat. Rev. Immunol. 9, 57-62 (2009).
Gruver et al., "Immunosenescence of ageing," J. Pathol. 211, 144-156 (2007).
McElhaney, "Influenza vaccine responses in older adults," Ageing Res. Rev. 10, 379-388 (2011).
Carr, E. J. et al., "The cellular composition of the human immune system is shaped by age and cohabitation. Nat. Immunol," 17, 461-468 (2016).
Nikolich-Žugich, "The twilight of immunity: emerging concepts in aging of the immune system," Nat. Immunol. 19, 10-19 (2018).
Ló Pez-Otin, "The hallmarks of aging. Cell," 153, 1194-1217 (2013).
Franceschi, C. et al., "Inflamm-aging. An evolutionary perspective on immunosenescence," Ann. N. Y. Acad. Sci. 908, 244-254 (2000).
Shen-Orr et al., "Defective signaling in the JAK-STAT pathway tracks with chronic inflammation and cardiovascular risk in aging humans," Cell Syst. 3, 374-384.e4 (2016).
Furman, D. et al., "Expression of specific inflammasome gene modules stratifies older individuals into two extreme clinical and immunological states," Nat. Med. 23, 174-184 (2017).
Orrù, V. et al., "Genetic variants regulating immune cell levels in health and disease," Cell 155, 242-256 (2013).
Patin, E. et al., "Natural variation in the parameters of innate immune cells is preferentially driven by genetic factors. Nat. Immunol," 19, 302-314 (2018).
Roederer, M. et al., "The genetic architecture of the human immune system: a bioresource for autoimmunity and disease pathogenesis," Cell 161, 387-403 (2015).
Brodin, P. et al., "Variation in the human immune system is largely driven by non-heritable Influences," Cell 160, 37-47 (2015).
Tsang, "Utilizing population variation, vaccination, and systems biology to study human immunology," Trends Immunol. 36, 479-493 (2015).
Shen-Orr et al., "Variability in the immune system: Of vaccine responses and immune states," Curr. Opin. Immunol. 25, 542-547 (2013).
Brodin et al., "Human immune system variation," Nat. Rev. Immunol. 17, 21-29 (2017).
Kaczorowski et al., "Continuous immunotypes describe human immune variation and predict diverse responses," Proc. Natl Acad. Sci. USA 114, E6097-E6106 (2017).

(Continued)

*Primary Examiner* — Michael V Meller
(74) *Attorney, Agent, or Firm* — Barnes & Thornburg LLP; G. Peter Nichols

(57) ABSTRACT

A method of reducing systemic chronic inflammation in a subject by administering a composition capable of reducing the expression level of inflammatory biomarkers.

1 Claim, 11 Drawing Sheets

(56) References Cited

OTHER PUBLICATIONS

Horvath et al, "An epigenetic clock analysis of race/ethnicity, sex, and coronary heart disease," Genome Biol. 17, 171 (2016).
Clegg et al., Frailty in elderly people. Lancet 381, 62167-62169 (2013).
Nakaya et al., "Systems analysis of immunity to influenza vaccination across multiple years and in diverse populations reveals shared molecular signatures," Immunity 43, 1186-1198 (2015).
Bektas et al., "Aging, inflammation and the environment," Exp. Gerontol. 105, 10-18 (2018).
Pawelec, "Immune parameters associated with mortality in the elderly are context-dependent: lessons from Sweden, Holland and Belgium," Biogerontology 19, 537-545 (2018).
Lin, Y. et al., "Changes in blood lymphocyte numbers with age in vivo and their association with the levels of cytokines/cytokine receptors," Immun. Ageing 13, 24 (2016).
Dai, et al., "A modified generalized Fisher method for combining probabilities from dependent tests," Front. Genet. 5, 32 (2014).
Furman, D. et al., "Apoptosis and other immune biomarkers predict influenza vaccine responsiveness," Mol. Syst. Biol. 9, 659 (2013).
Merino, J. et al., "Progressive decrease of CD8high+ CD28+ CD57− cells with ageing," Clin. Exp. Immunol. 112, 48-51 (1998).
Afzali, B. et al., "CD161 expression characterizes a subpopulation of human regulatory T cells that produces IL-17 in a STAT3-dependent manner," Eur. J. Immunol. 43, 2043-2054 (2013).
Haghverdi et al., "Diffusion pseudotime robustly reconstructs lineage branching," Nat. Methods 13, 845-848 (2016).
Shen-Orr, S. S. et al., "Defective signaling in the JAK-STAT pathway tracks with chronic inflammation and cardiovascular risk in aging humans," Cell Syst. 3, 374-384.e4 (2016).
D'Agostino, R. B. et al., "General cardiovascular risk profile for use in primary care: The Framingham Heart Study," Circulation 117, 743-753 (2008).
Barbie, D. A. et al., "Systematic RNA interference reveals that oncogenic KRAS-driven cancers require TBK1," Nature 162, 108-112 (2009).
Horvath, S., "DNA methylation age of human tissues and cell types," Genome Biol. 14, R115 (2013).
Marioni, R. E. et al., "DNA methylation age of blood predicts all-cause mortality in later life," Genome Biol. 16, 25 (2015).
Novershtern, "Interconnected transcriptional circuits control cell states in human hematopoiesis," Cell 144, 296-309 (2011).
Pawelec, G., "Immune parameters associated with mortality in the elderly are context-dependent: lessons from Sweden, Holland and Belgium," Biogerontology 19, 537-545 (2018).
Ridker, P. M. et al., "Antiinflammatory therapy with canakinumab for atherosclerotic disease," N. Engl. J. Med. 377, 1119-1131 (2017).
Blazkova, J. et al., "Multicenter systems analysis of human blood reveals immature neutrophils in males and during pregnancy," J. Immunol. 198, 2479-2488 (2017).
Furman, D. et al., "Systems analysis of sex differences reveals an immunosuppressive role for testosterone in the response to influenza vaccination," Proc. Natl Acad. Sci. USA 111, 869-874 (2014).
Furman, D. et al., "Cytomegalovirus infection enhances the immune response to influenza," Sci. Transl. Med. 7, 281ra43 (2015).
International Search Report and Written Opinion issued in PCT/US2022/038704 on Nov. 23, 2022.
Koenig et al., "Avenanthramide Supplementation Attenuates Exercise-Induced Inflammation in Postmenopausal Women," Nutritional Journal, Biomed Central, GB, vol. 13, No. 1, Mar. 19, 2014, pp. 21.
Wolever et al., "An Oat [beta]-Glucan Beverage Reduces LDL Cholesterol and Cardiovascular Disease Risk in Men and Women with Borderline High Cholesterol: A Double-Blind, Randomized, Controlled Clinical Trial," The Journal of Nutrition, vol. 151, No. 9, Jun. 3, 2021, pp. 2655-2666.
Dioum, et al., "Oats Lower Age-Related Systemic Chronic Inflammation (iAge) in Adults at Risk for Cardiovascular Disease," Nutrients, Oct. 25, 2022.
Emmons et al., "Antioxidant Capacity of Oat (*Avena sativa* L.) Extracts. 2. in Vitro Antioxidant Activity and Contents of Phenolic and Tocol Antioxidants," Journal of Agricultural and Food Chemistry, American Chemical Society, US., vol. 47, No. 12, Dec. 1, 1999 (Dec. 1, 1999), pp. 4894-4898, XP008070121, ISSN: 0021-8561, DOI: 10.1021/JF9905301.
Examination Report issued in EP 22757754.1 on Dec. 19, 2024.

\* cited by examiner

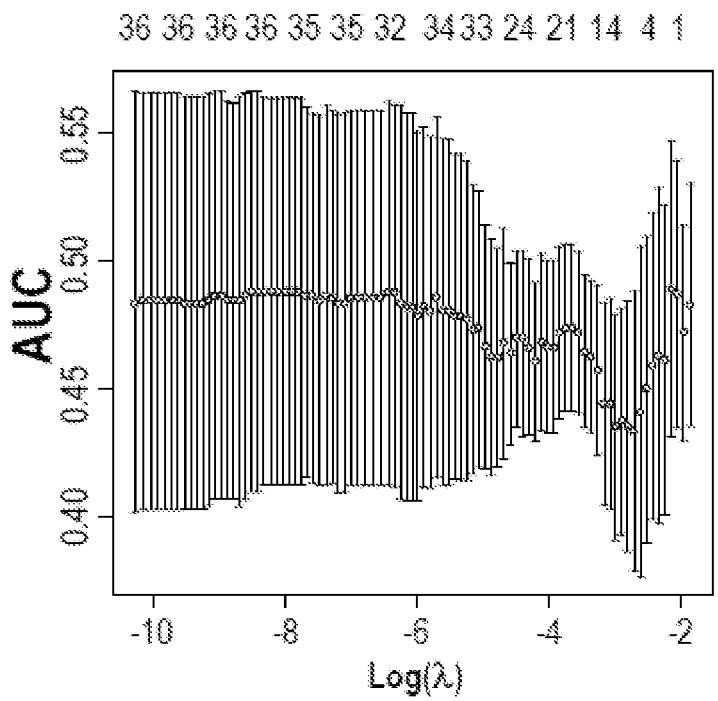
Fig. 2C
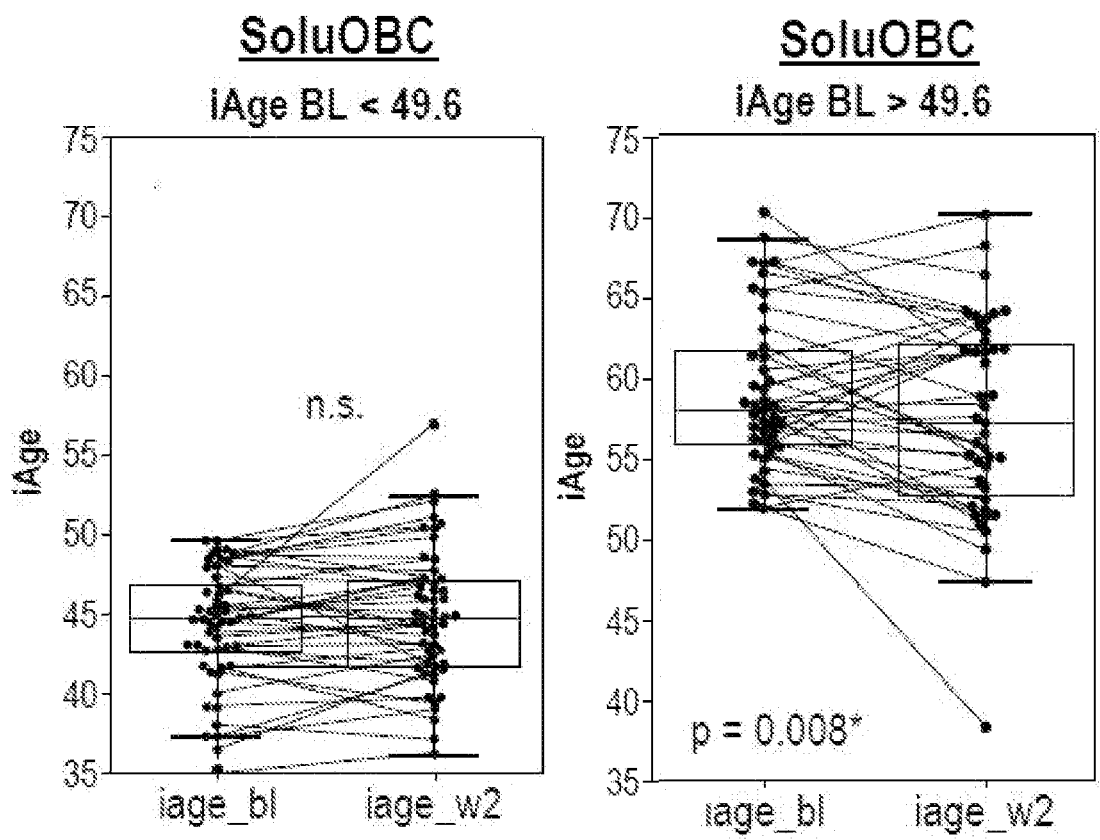
Fig. 3A
Fig. 3B

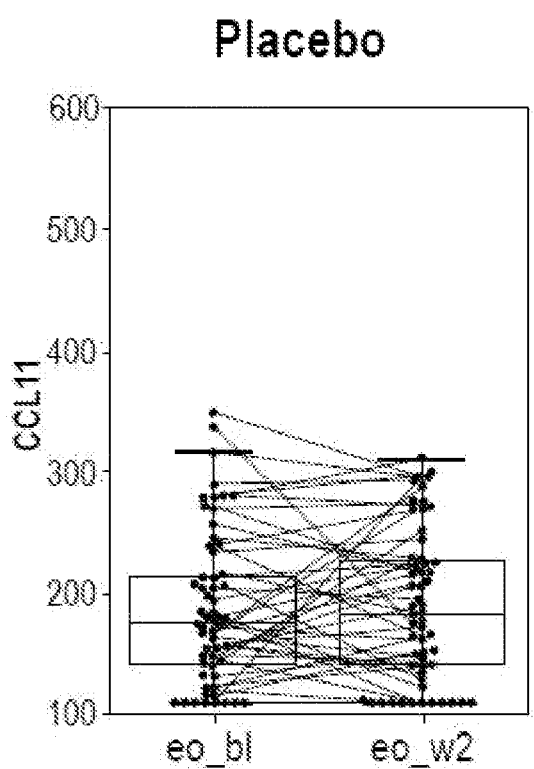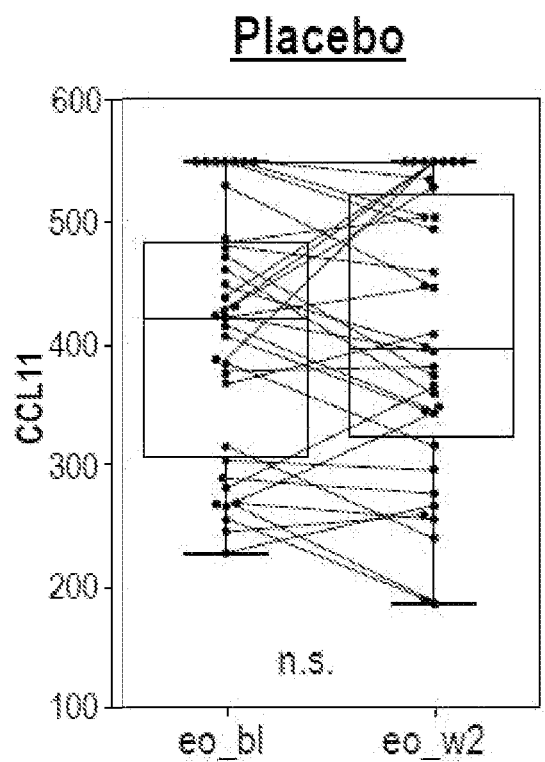
Fig. 3G
Fig. 3H

METHOD OF REDUCING AGE-RELATED SYSTEMIC CHRONIC INFLAMMATION

This application claims priority to U.S. Application No. 63/226,553 filed Jul. 28, 2021, the entire contents of which are incorporated herein by reference.

The present disclosure relates generally to the reduction of age-related chronic inflammation. More specifically, the present disclosure relates to a method of reducing systemic chronic inflammation by administering an effective amount of β-glucan, avenanthramides, or other phenolics.

BACKGROUND

Systemic chronic inflammation (SCI) can lead to a myriad of age-related chronic diseases. The National Council on Aging and the Centers for Disease Control and Prevention estimate that more than 80% of the population 65 years and older have at least one chronic condition, 69% are afflicted by 2 or more chronic diseases and 34% have 4 or more chronic diseases. The implications of systemic chronic inflammation can be severe and include elevated risk of type 2 diabetes, hypertension, cardiovascular disease, chronic kidney disease, cancer, depression, neurodegenerative and autoimmune diseases, and osteoporosis.

Inflammation is a highly conserved defensive mechanism capable of eliminating microorganisms and repairing tissue. It is characterized by the activation of immune and non-immune cells that provide surveillance and protection against a full spectrum of microorganisms and toxic insults. Normal inflammatory responses are represented by acute and time-limited upregulation of the innate inflammatory response. Typically, this acute innate immune response is short and self-resolves once the threat has been eliminated.

Although sharing some common mechanisms, the acute innate inflammatory response differs from SCI in several important ways. In contrast with the acute short-lived inflammatory response, SCI or "inflammaging" is a major characteristic of the aging process. It is believed that SCI is initiated by unresolved triggers of acute inflammation or physical, chemical, or metabolic noxious stimuli (i.e., "sterile" agents), released by damaged cells or environmental insults that are generally called damage-associated molecular patterns (DAMP). These DAMPS promote a state of low-grade, systemic chronic inflammation characterized by the activation of immune components that are distinct from those triggered during an acute immune response.

A novel metric for SCI was developed from a ten-year project across 1,000 subjects at Stanford University called the 1,000 Immunomes Project (1KIP). This metric was derived from a deep learning algorithm applied to immune protein serum biomarkers. The Stanford 1KIP focused on global analysis of the immune system and utilized state-of-the-art deep learning tools to construct a scoring system for age-related chronic inflammation (Inflammatory Age®, iAge®) which predicted multi-morbidity, premature cardiovascular aging, immunological decline, frailty and all-cause mortality. Some of the biomarkers of iAge® identified in the Stanford 1KIP include CCL11 (Eotaxin), Interferon-gamma (IFN-γ), Growth Regulated Oncogene-alpha (Gro-α), Monokine Induced by Gamma Interferon (CXCL9) and TNF-related Apoptosis Inducing Ligand (TRAIL).

Chronic inflammation, inflammatory disease and infection can induce a broad range of deficits in lipid metabolism, including decreases in serum HDL, increases in triglycerides, lipoprotein a (Lp(a)) and low density lipoprotein (LDL). The sustained levels of inflammation resulting from changes in lipid homeostasis is a contributor to atherosclerosis risk. In addition to affecting serum lipid levels, SCI can adversely affect lipoprotein function. For instance, the ability of high density lipoprotein (HDL) to prevent oxidation of LDL is severely diminished and several steps in reverse cholesterol efflux are also affected by the activation of the immune system. It is now established that soluble and cellular immune factors associated with SCI can promote inflammation-related endothelial dysfunction and atherogenesis. Therefore, individuals with elevated iAge® and LDL cholesterol levels represent a population at risk for CVD and other vascular complications.

A need exists to prevent or reduce systemic chronic inflammation and slow biological aging in subjects.

SUMMARY

Aspects and embodiments of the present invention are set out in the appended claims. These and other aspects and embodiments of the invention are also described herein.

Chronological age and biological age are two separate metrics used to understand diseases associated with aging. While science has yet to figure out how to reverse chronological age, some breakthroughs have shown that it is possible to slowdown, or even reverse, biological aging. There are many possible variables that can impact biological age including: chronological age, genetics, gender, geographic locations, socio-economic status, exposure to environmental insults, sleep habits, exercise, and of course, diet. Sifting through the enormous amount of data to identify specific impactors has been challenging. The following describes a method that applies a recent discovery to stall or reverse the biological age of a subject by reducing the level of systemic chronic inflammation (SCI) biomarkers.

The method to reduce SCI includes administering to a subject an effective amount of a composition that includes selected ingredients to reduce the expression level of biomarkers associated with systemic chronic inflammation.

The method takes advantage of the discovery of biomarkers that correlate with increased inflammation. Initial SCI biomarkers were identified based on those used in an algorithm called iAge® that calculates a biological age of a subject based on the levels of certain SCI biomarkers. For example, a person having a chronological age of 50 may have a biological age of less than 50 or greater than 50 depending on the subject's expressed levels of certain SCI biomarkers. Accordingly, while the chronological age cannot change, the biological age of a subject can fluctuate up or down over time depending on a variety of variables.

The composition may be provided as a powder capable of being encapsulated such as in a biodegradable capsule. The composition may be provided as a loose powder capable of being added or incorporated into foodstuff or beverages. In all forms, the composition may be configured to be ingested by a subject.

The invention extends to methods, systems, or kits of parts substantially as described herein and/or as illustrated with reference to the accompanying figures and description.

The invention extends to any novel aspects or features described and/or illustrated herein. In addition, apparatus aspects may be applied to method aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

BRIEF DESCRIPTION OF THE DRAWINGS

The following description accompanies the drawings, all given by way of non-limiting examples that may be useful to understand how the described process and system may be embodied.

FIG. 2C is a graph showing that none of an initial 39 variables appear to be useful to predict responders and non-responders within the untreated group.

FIG. 3A is a graph showing the comparison of iAge® at baseline to week two for the treated group having an initial baseline iAge® score less than 49.6.

FIG. 3B is a graph showing the comparison of iAge® at baseline to week two for the treated group having an initial baseline iAge® score greater than 49.6.

FIG. 3G is a graph comparing the CCL11 level at baseline to week two for the untreated group having an initial baseline iAge® score is less than 49.6

FIG. 3H is a graph comparing the CCL11 level at baseline to week two for the untreated group having an initial baseline iAge® score is greater than 49.6.

DETAILED DESCRIPTION

Figure 1A:
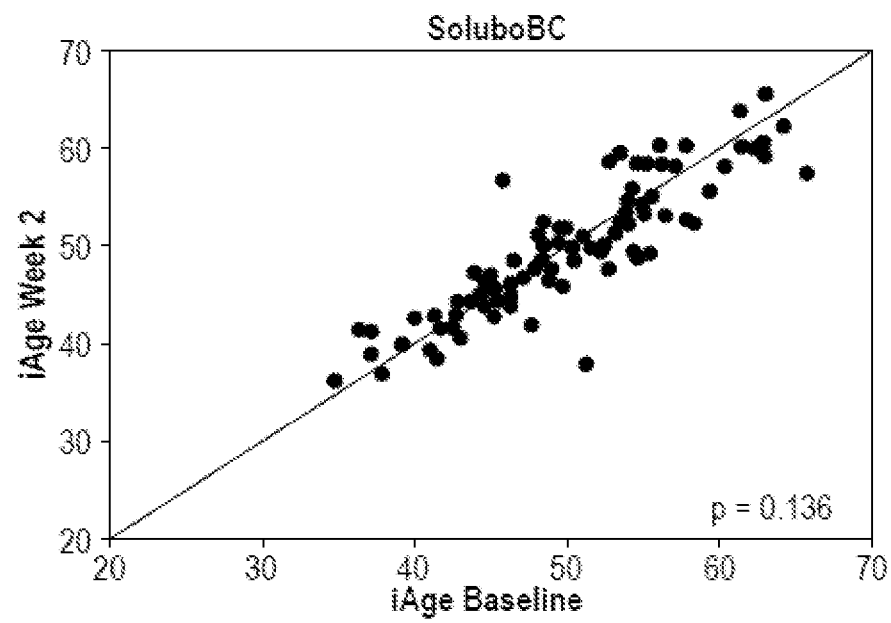
FIG. 1A is a graph comparing the baseline (day 0) iAge® to the week two iAge® for the treated group.
Figure 1B:
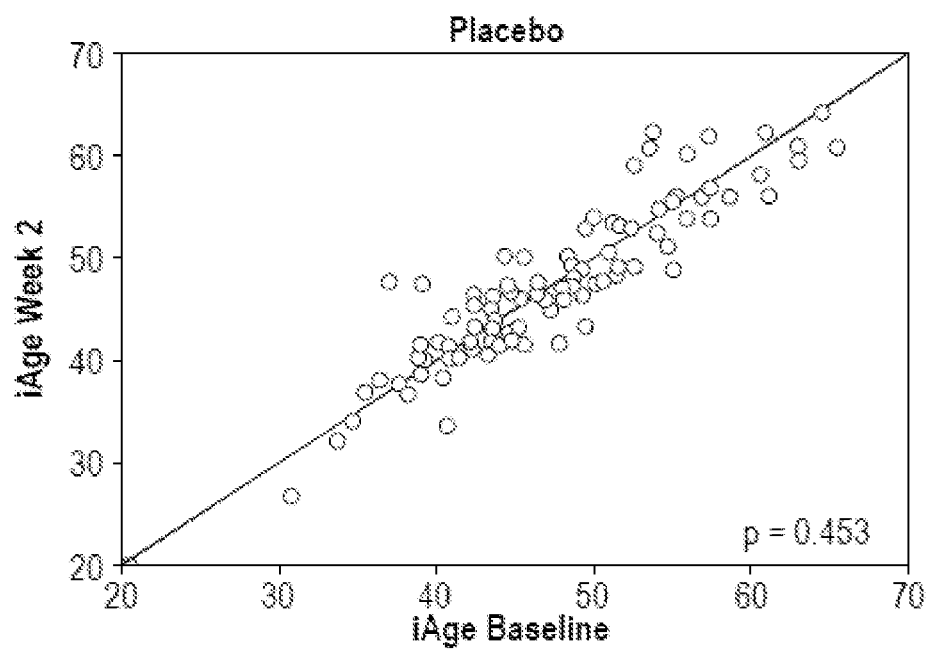
FIG. 1B is a graph comparing the baseline iAge® to the week two iAge® for the untreated group.

A method for reducing systemic chronic inflammation (SCI) in a subject that includes administering an effective amount of a composition to a subject is described.

The subject may be a mammal, and more particularly a human. The subject may have low-density lipoprotein (LDL) cholesterol levels of at least about 3 mmol/L. The LDL cholesterol level may be between about 3 mmol/L to about 5 mmol/L. In some embodiments, the LDL cholesterol level is at least about 3 mmol/L, about 3.1 mmol/L, about 3.2 mmol/L, about 3.3 mmol/L, about 3.4 mmol/L, about 3.5 mmol/L, about 3.6 mmol/L, about 3.7 mmol/L, about 3.8 mmol/L, about 3.9 mmol/L, or at least about 4 mmol/L. The subject's LDL cholesterol level may be at least about 3.25 mmol/L, about 3.26 mmol/L, about 3.27 mmol/L, about 3.28 mmol/L, about 3.29 mmol/L, about 3.3 mmol/L, or at least about 3.3 mmol/L.

The subject may have a biological age (also referred to as an iAge® score) of at least about 45. An iAge® score is calculated using a method and parameters disclosed in U.S. Patent Application Publication 2021/0109109 published Apr. 15, 2021, the entire contents of which are incorporated herein by reference. The biological age is generated using a guided auto-encoder algorithm that assigns weighted scores to the amount of the five biomarkers (Eotaxin-1 (CCL11), IFNγ, Gro-α, MIG, and TRAIL). The subject's biological age may be between 45 and 115. In some aspects, the subject's biological age may be at least about 45, 46, 47, 48, 49, 50, 51, or 52. In some embodiments, the subject's biological age may be at least 49.1, 49.2, 49.3, 49.4, 49.5, 49.6, 49.7, 49.8, 49.9, or 50.

Briefly, the iAge® algorithm was generated as follows. Blood and serum samples were collected from 1000 participants. Input data consisted of serum protein micro-flow imaging (MFI) and cell subpopulation frequency data. The data was first log-transformed and then 6 different distributions (Normal, Laplace, LogNormal, log-Laplace, Gamma, log-Gamma) were fit on each input feature using max likelihood estimation (MLE). To identify the best distribution for each feature, a five-fold-cross-validation test was performed for each distribution. A t-test p-value was calculated for the five-fold test likelihoods between normal distribution and other distribution.

Identification of Immunotypes: Agglomerative clustering on the processed cell subpopulation data was performed. To identify the best cluster number, gap-statistic is used. The gap-statistic utilizes bootstrap to estimate the cluster quality, which is the improvement compared to a null hypothesis that the data is uniformly distributed. Bootstrap chooses the smallest number of clusters when adding another cluster would not provide significant increase in cluster quality. With a 1000-sample bootstrap test, the best number of clusters was 16. Hence, an agglomerative clustering with 16 clusters is performed on the data, to identify 16 immune sub-types.

Immunological analysis of immunotypes. Immune protein data (50 cytokines, chemokines and growth factors: MIG, TRAIL, IFNG, EOTAXIN (i.e., CCL11), GROA, IL2, TGFA, PAI1, MIP1A, LEPTIN, IL1B, LIF, IL5, IFNA, IL4, NGF, HGF, VEGF, FGFB, TGFB, MCSF, PDGFBB, IL7, GMCSF, IL12P40, IL8, SCF, GCSF, CD40L, MIP1B, IL12P70, RESISTIN, IFNB, RANTES, TNFA, MCP1, IL17F, ENA78, IL1RA, IL10, IP10, IL13, IL1A, IL15, ICAM1, TNFB, IL6, MCP3, VCAM1, and FASL) available for all 1001 subjects were used and ex vivo signaling responses to cytokine stimulation data (84 different cytokine-cell-phosphoprotein combinations) available for a total of 818 subjects were used. For the development of a signature that differentiates each immunotype, prediction analysis of microarrays (PAM) was used to create a classifier in a training set with subsequent validation in a test set. Prediction analysis of microarrays is a statistical technique that creates a phenotype-specific "nearest shrunken centroid" for classification, and can be used to compare the levels of each immune feature across immunotypes. This is done by a balanced 10-fold cross-validation in a training set, which enables one to choose a threshold that minimizes classification errors. This method makes one important modification to standard nearest centroid classification; it "shrinks" each of the immunotype centroids toward the overall centroid for all immunotypes, which confers an advantage since it makes the classifier more accurate by reducing the effect of the noisy features. The comparison in the levels of serum proteins or signaling responses of specific immunotypes (e.g., 13, 14 and 16) was done by self-contained test of modified Fisher's combined probability on the raw data.

Clinical analysis of immunotypes: For each disease, a logistic regression model penalized with l1 penalty was fit using predictors: gender, age, BMI and dummy variable for an immunotype. The training procedure for the penalized logistic regression used cross-validation over 3 folds to select the weight of l1 penalty. In order to assess the significance of the model's parameters, a permutation test was performed. Disease assignments to patients 1000 times were permuted. For each such permutation, the same fitting procedure was used to obtain the penalized logistic regression weights. It was assessed how often the weights learned on the real data exceeded, in absolute value, the weights computed on the permuted data. The frequency of this occurrence as empirical p-value was reported.

Metabolic gene modules analysis: A module analysis is performed on the metabolic genes from a sub-cohort of 394 patients. There were 851 genes that overlapped with the metabolic gene set. Agglomerative clustering was used with 50 clusters on the standardized log-transformed metabolic gene expression levels. For each cluster, the Spearman's correlation coefficient was calculated and p-value was obtained between all the gene expression level and patients' age.

Guided Auto-Encoder (GAE) and SCI: When dealing with the data with a large number of dimensions, a goal was to find a reasonable way to summarize the data possibly to a compact representation. This compact representation can be further used for feature extraction, visualization, or classification purpose. To obtain the informative representation, a novel model called "Guided Auto-Encoder" was proposed. It was built based on Auto-Encoder with a combined objective. Auto-encoders use a non-linear transformation of the data. Hence, it can model more complex processes. One problem of auto-encoders is re-parameterization. With different initialization, it could have different results. Among the different types of visualizations with similar summarization levels, one usually wants a representation that is informative of a specific target. Hence, a representation with two focuses can be constructed: 1) the learned compact representation h can be recovered to the original data as much as possible (reconstruction loss); 2) the learned compact representation should be as informative of the desired target as possible (prediction loss). Therefore, a novel structure—guided-auto-encoder—that balances the two objectives in order to provide an informative representation was proposed. The GAE to extract SCI was applied. It is a non-linear transformation of the cytokine data in a person that both approximates the true age, while preserving the information of the cytokine level.

Auto-encoder: Given the input data vector x, an auto-encoder aims to reconstruct the input data vector x. An auto-encoder with L encoding layers and L decoding layers has depth of L were considered, and each layer has fixed number of hidden nodes m.

For convenience, the input layer is defined as $h_0(x)=x$, and the output of lth hidden layer is defined as $h_l(x)$. The number of nodes in layer l is $m_l$. The input into the lth layer of the network is defined as:

$$a_l(x) = h_{l-1}(x)^T W_l + \beta_l,$$

where Wi is a real value weight matrix of by $m_{l-1}$ and $\beta_l$ is a vector of length $m_{l-1}$. The output of lth hidden layer is:

$$h_l(x) = \tan h(a_l(x))$$

where tan h is the hyperbolic tangent function:

$$\tanh(x) = \frac{1-e^{-2x}}{1+e^{-2x}}$$

The output of the Lth layer $h_L(x)$ as the coding layer was defined. The decoding layers are from L+1 to 2L−1 layer with the same setting. Finally, a linear output layer is on top of the last decoding layer:

$$f_{AE}(x) = h_{2L-1}(X)^T W_{2L-1} + \beta_{2L},$$

Given data vectors x, an auto-encoder was trained, the reconstruction loss on the data was minimized:

$$\text{minimize}_\theta \sum_i \left\| f_{AE}(x^i, \theta) - x^i \right\|_2^2 + \lambda \|\theta\|_2^2$$

where i ranges of the number of samples, θ represents all the parameters used in the auto-encoder, and λ is the weight decay penalty used for regularization. To optimize the objective (1), a stochastic optimization method ADAM was used.

Figure 7:
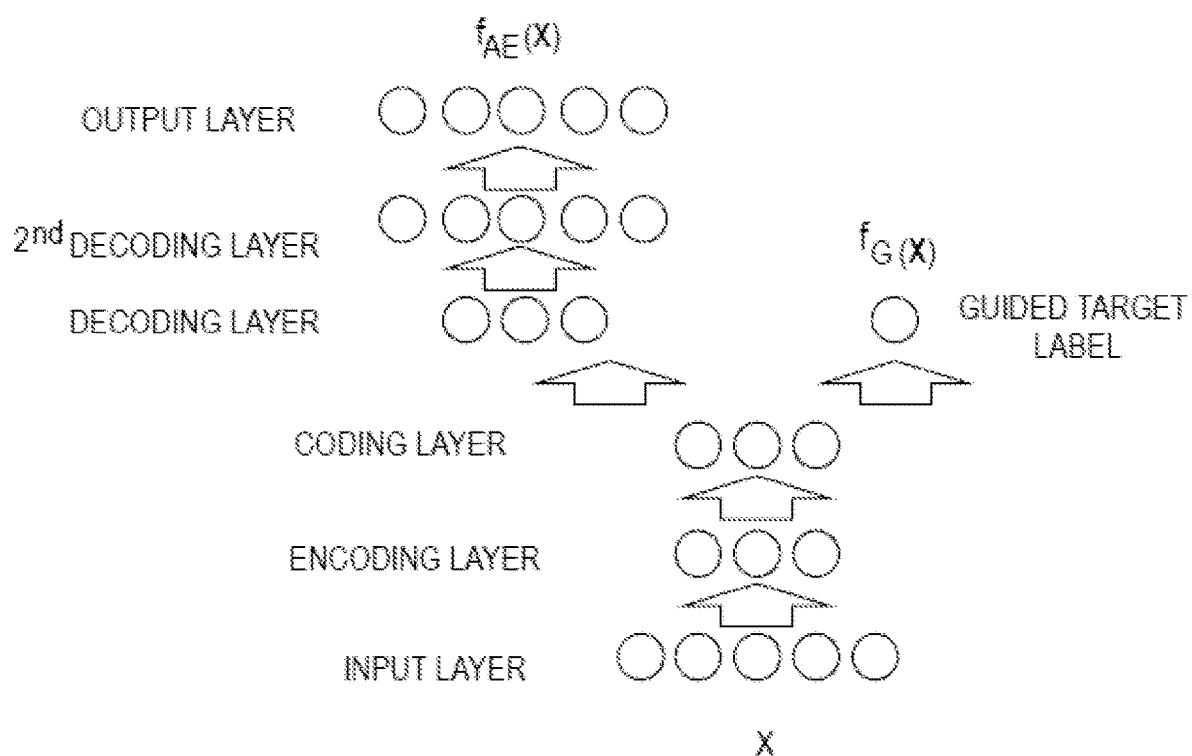
FIG. 7 shows a graphic representation of an exemplary guided-auto-encoder.

Guided-Auto-encoder: A guided auto-encoder aims to reduce both the reconstruction loss and predictive loss. Given the input x, a side-phenotype y and an auto-encoder $f_{AE}$, the guided-auto-encoder incorporates a predictive function on the coding layer:

$$f_G(x) = h_L(x)^T w_G + \beta_G,$$

with its own set of parameters $w_G$ and $\beta_G$.
Let θ be the set of all parameters of a GAE, the training objective is:

$$\text{minimize}_\theta \Sigma_i (\alpha \|f_G(x^i,\theta)-y^i\|_2^2 + (1-\alpha)\|f_{AE}(x^i,\theta)-x^i\|_2^2) + \lambda\|\theta\|_2^2, \quad (2)$$

where α is a real value number between 0 and 1 that is called the guidance-ratio. An example guided-auto-encoder with depth 2 and width 3 is shown in FIG. 7.

Optimization method ADAM was used to minimize objective. By choosing different guidance-ratio(s), different level(s) of balance can be reached between prediction loss and reconstruction loss.

Extraction of SCI: In order to provide a marker summarization of a patient's immune system health state, a novel quantity—SCI was invented. This quantity is the age of patient predictable from the state of the immune system. In order to obtain this quantity cytokine measurements were focused on. By construction, the SCI is a non-linear function of cytokine measurements, but also an estimate of the patient's true age.

To construct this quantity, Guided Auto-Encoder (GAE), which was aimed to compactly represent cytokine measurements and predict side-phenotype chronological age, was used. The best code length was identified, among lengths from 1 to 10, using a five-fold-cross-validation. The length of code k, whose performance was not statistically significantly worse than that of longer codes (paired t-test p-value>0.05) was selected. Within each fold nested three-fold cross-validation was performed to select hyper-parameters (depth, weight decay and guidance-ratio).

After obtaining the best code length as 5, the five-fold-cross-validation was used to select the best hyper-parameter setting (depth=2, guidance-ratio=0.2, L2=0.001) on all GAE with code length 5. Finally, the GAE was trained on the whole dataset with the selected best hyper-parameter setting, and obtained the predictive function as the SCI predictor.

Data and Software Availability

Data availability: The cell subpopulation, immune protein and cell signaling data for the Stanford Aging and Vaccination studies are publicly available on ImmPort Bioinformatics Repository under the following study IDs SDY311 (cytokines, phosphoflow assays and CyTOF surface phenotyping), SDY312 (cytokines, phosphoflow assays and flow cytometry surface phenotyping), SDY314 (flow cytometry surface phenotyping), SDY315 (cytokines, phosphoflow assays and CyTOF surface phenotyping) and SDY478 (cytokines and CyTOF surface phenotyping).

The subject may have an LDL cholesterol level of at least about 3 mmol/L or an iAge® of at least about 45. Alternatively, the subject may have an LDL cholesterol level of at least about 3 mmol/L and an iAge of at least about 45. The subject may have an iAge® of at least 49 or an LDL cholesterol level of at least 3.2 mmol/L. Alternatively, the subject may have an iAge® of at least 49 and an LDL cholesterol level of at least 3.2 mmol/L.

Reducing SCI refers to reducing the expression level of proteins associated with inflammation. A reduction in the expression level of proteins associated with inflammation can be demonstrated by comparing the expression levels of proteins in a subject before administering the composition and after administration of the composition. In some embodiments, the reduction in expression level of proteins associated with inflammation may be detectable after administering the effective amount of the composition every day to a subject for at least one week, at least two weeks, at least three weeks, or at least four weeks.

In some instances, the method may reduce the expression level of Eotaxin-1 (i.e., CCL11), IFNγ, Gro-α, MIG, or TRAIL in a subject. The method may reduce the expression level of CCL11 and at least one other protein selected from the group consisting of IFNγ, Gro-α, MIG, and TRAIL. When the expression level of CCL11, IFNγ, Gro-α, MIG, or TRAIL is reduced in a subject, the subject's biological age may also reduce. Additionally, once the expression level of proteins associated with inflammation are reduced, a subject's biological age may be reduced. For example, after receiving the effective amount of a composition every day for about four weeks, the subject's biological age may reduce by about one year, about two years, about three years, or about four years based on the iAge® algorithm. In some embodiments, a subject's biological age reduces by at least about one year, at least about two years, at least about three years, or at least about 4 years.

Additionally, by reducing SCI in a subject, the method may treat or prevent disease-associated conditions such as neuroinflammation, neurodegeneration, or psychiatric disorders. The method may be used to lower LDL cholesterol to treat or prevent disease associated with central nervous system pathophysiology.

The composition may be provided in a form for oral consumption by the subject. For example, the composition may be provided as a powder capable of being encapsulated such as in a biodegradable capsule. The composition may also be provided as a loose powder capable of being added or incorporated into foodstuff or beverages. Additionally, the composition may be incorporated into a foodstuff or a beverage prior to being administered to a subject.

The effective amount of the composition is the minimum amount needed to reduce systemic chronic inflammation in a subject. The effective amount may be capable of reducing the biological age and/or reducing the expression level of proteins associated with inflammation in the subject. The effective amount of the composition may be administered in a single administration or provided in total over several administrations, such as two, three, or four times a day. For example, the effective amount may be about 2 g to about 5 g total for a single day of beta-glucan, which may be divided over several administrations (two, three, four, or five) throughout the day.

The effective amount of beta-glucan provided to a subject in a single day may be at least about 2 g. The effective amount of beta-glucan provided to a subject in a single day may be between about 2 g to about 5 g, about 2 g to about 6 g, about 3 g to about 6 g, about 3 g to about 5 g, or about 3 g to about 4 g. The effective amount of avenanthramides provided to a subject in a single day may be at least 0.5 mg. The effective amount of avenanthramides provided to a subject in a single day may be between about 0.5 mg to about 3 mg, about 1 mg to 3 mg, or about 1 mg to about 2 mg.

The composition may include beta-glucan, avenanthramides, phenols, or a combination of such. The source of beta-glucan, avenanthramides, or phenols may be provided from natural or synthetic sources. The composition may have beta-glucan and at least one additional component selected from avenanthramides or phenols. In some aspects, the composition includes beta-glucan, avenanthramides, and phenols.

The composition may contain at least about 0.75 g of beta-glucan. In some embodiments, the composition may contain about 1.0 g, about 1.5 g, about 2.0 g, about 2.5 g, about 3.0 g, about 3.5 g, about 4 g, about 4.5 g, or about 5 g of beta-glucan. The composition may have between about 0.75 g to about 10 g, about 1 g to about 8 g, or about 2 g to about 5 g of beta-glucan. In some aspects, the composition has about 0.75 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g. The composition may have about 3 g of beta-glucan.

As noted above, the composition may contain avenanthramides. When avenanthramides are included, the composition may include at least about 0.5 mg of avenanthramides. In some aspect, the composition includes at least about 0.5 mg, at least about 1 mg, at least about 1.5 mg, or at least about 2 mg of avenanthramides. The composition may include between about 0.5 mg and about 2.0 mg of avenanthramides. In some embodiments, the composition has about 0.90 mg, about 0.95 mg, about 1.0 mg, about 1.05 mg, about 1.10 mg, about 1.15 mg, about 1.20 mg, about 1.25 mg, about 1.30 mg, about 1.35 mg, about 1.40 mg, about 1.4 mg, or about 1.50 mg. The composition may contain 1.10 mg, 1.11 mg, 1.12 mg, 1.13 mg, 1.14 mg, 1.15 mg, 1.16 mg, 1.17 mg, 1.18 mg, 1.19 mg, or 1.20 mg of avenanthramides.

The avenanthramides may include the A, B, and/or C forms. The percentage by weight of avenanthramide A may range from about 1% to about 98% of the total avenanthramides percentage by weight. The percentage by weight of avenanthramide B may range from about 1% to about 98% of the total avenanthramides percentage by weight. Additionally, the percentage by weight of avenanthramide C may range from about 1% to about 98% of the total avenanthramides percentage by weight. In one example, avenanthramide A, B, and C may be present in the composition in about equal amounts of 33.3% by weight.

The composition may include phenolics such as Avenanthramide A, B, and/or C, Ferulic acid, Caffeic acid, Sinapic acid, gallic acid, 4-hydroxybenzoic acid, 2,4-dihydroxybenzoic acid, 4-hydroxyphenyl acetic acid, vanillic acid, 4-hydroxybenzaldehyde, homovanillic acid, syringic acid, p-coumaric acid, vanillin, Salicylic acid, syringaldehyde, sinapic acid, 3-5, dichloro-4-hydroxybenzoic acid, and o-coumaric acid, or such a combination.

The composition may have at least about 20 mg of total phenolics. The composition may have at least about 20 mg, 25 mg, 30 mg, 35 mg, 40 mg, 45 mg, 50 mg, 55 mg, or 60 mg of total phenolics. The composition may contain between about 20 mg to about 65 mg, about 30 mg to about 55 mg, or about 40 to about 50 mg of total phenolics. In some embodiments, the composition includes 46.0 mg, 46.1 mg, 46.2 mg, 46.3 mg, 46.4 mg, 46.5 mg, 48.7 mg, 46.8 mg, 46.9 mg, or 47 mg of total phenolics.

The composition may include at least about 2 g of beta-glucan or at least about 45 mg of total phenolics. The composition may include about 2.5 g of beta-glucan and at least about 40 mg of total phenolics. In some aspects, the composition includes at least 3 g of beta-glucan and at least 46 mg of total phenolics.

In one illustrative embodiment, the effective amount of the composition may include at least about 3 g of beta-glucan, at least about 2.6 mg total phenolics, and at least about 1.14 mg of avenanthramides per day provided to the subject. The effective amount may be administered at least once a day, or divided to be administered twice a day, three times a day, four times, or five times per day. Alternatively, the composition may be administered every-other day.

The method may include providing the effective amount of beta-glucan per day for at least about 1 week, about 2 weeks, about 3 weeks, or at least about 4 weeks. The effective amount of beta-glucan per day may be administered based on a dosing regimen. The dosing regimen may occur for about one week to about 8 weeks, about two weeks to about 8 weeks, about 2 weeks to about 6 weeks, or about 2 weeks to about 4 weeks. For example, a subject may be administered a composition three times a day to provide a total amount of beta-glucan of 3 g over the course of that day. The three times a day administration may occur during the length of a dosing regimen of at least about one week, at least about 2 weeks, at least about 3 weeks, at least about 4 weeks, or at least about 5 weeks. In some embodiments, a subject orally consumes the composition containing an effective amount of beta-glucan and avenanthramides each day for a dosing regimen that occurs for the rest of the subject's life.

The composition may be provided as a plant based material having partially hydrolyzed starch. The partially hydrolyzed starch may comprise at least about 50% of the total starch content. The hydrolyzed starch molecules may have an average molecular weight of no more than $3.4 \times 10^6$ (optionally, $3.0 \times 10^6$, $2.5 \times 10^6$, $2.0 \times 10^6$, $1.8 \times 10^6$, $1.7 \times 10^6$, $1.6 \times 10^6$, $1.5 \times 10^6$, $1.4 \times 10^6$, $1.37 \times 10^6$) Dalton, or equal to about $3.6 \times 10^6$ to about $1.0 \times 10^6$.

In some embodiments, the composition is formed from oat bran having partially hydrolyzed starch. The composition may be an oat bran concentrate (commercially available as SoluOBC, PepsiCo Inc.) or a partially hydrolyzed oat flour.

Methods of preparing a partially hydrolyzed oat flour are provided in U.S. Pat. No. 9,510,614 issued Dec. 6, 2016, and incorporated herein by reference. Briefly, to prepare the composition, an oat flour may be combined with other ingredients and an enzyme (e.g., alpha-amylase) to partially hydrolyze the starch in the oat flour, while still maintaining the whole grain status of the oat. The mixture may be heated to between about 120° F. and about 200° F. The mixture may be mixed in a vessel such as an extruder. The enzyme is deactivated in the extruder to form the partially hydrolyzed oat flour. The partially hydrolyzed oat flour may be processed further such as addition of flavorings or stabilizers. The advantage of the partially hydrolyzed starch in the composition is that it can be easily incorporated into a beverage or a foodstuff for administering to a subject.

In one illustrative aspect of making a partially hydrolyzed oat flour, a whole oat flour starting mixture and a suitable enzyme solution in a mixer (sometimes called a pre-conditioner) and then heating the mixture. The enzyme-treated mixture is then subjected to an extrusion process to gelatinize, hydrolyze, and cook the oat flour mixture.

A suitable starting mixture is prepared by combining the whole oat flour with other desired ingredients. For example, a typical starting mixture contains whole oat flour and granulated sugar. Maltodextrin and/or at least one antioxidant may also be added.

The whole oat flour is present in an amount of about 50% to about 100% by weight of the total weight of the starting composition. In further aspects, the whole oat flour is present in amounts of about 80% to about 95% by weight or about 90% to about 95% by weight.

The sugar can be any suitable sugar known to those skilled in the art. Non-limiting examples of sugars include sucrose, fructose, dextrose, other sugars known in the art, and combinations thereof. Typically, the sugar is present in an amount of about 1% to about 15% by weight or about 3% to about 15% by weight of the total weight of the starting composition. In further aspects, the sugar is present in amounts of about 3% to about 7% by weight.

The maltodextrin may be present in an amount of about 0% to about 15% by weight of the total weight of the starting composition. In further aspects, the maltodextrin is present in amounts of about 3% to about 7% by weight.

The antioxidant may be any suitable antioxidant such as mixed natural tocopherols or artificial antioxidant such as BHT and BHA. The antioxidant is present in an amount from 0.1% to 2% by weight. In further aspects, the antioxidant is present in amounts of about 0.25% to about 0.75% by weight.

A suitable, but non-limiting, flour mix formula for extrusion process.

| Ingredient | % |
| --- | --- |
| Whole oat flour | 89.35 |
| Sugar | 5.00 |
| Maltodextrin | 5.00 |
| Mixed tocopherols | 0.50 |
| α-amylase | 0.15 |
| Total | 100.00 |

The enzyme may be any suitable enzyme to hydrolyze the starch in the oat flour and does not change or adversely affect the beta-glucan that is present in the oat flour. Suitable enzymes include α-amylase in the range of about 0.01% to about 0.5% by weight, for example about 0.1% to about 0.2% by weight. In one aspect of the present disclosure, the α-amylase used may be Validase 1000 L having approximately 1,000,000 MWU/g (MWU—Modified Wohlgemuth Unit). Whether the beta-glucan has changed by the hydrolysis can be determined by any suitable method such as by analyzing the structure of the beta-glucan. This can be done by laser light scattering mass spectroscopy. The enzyme is added to water to form an enzyme water solution. Then the enzyme-water solution is combined with the starting mixture in the pre-conditioner.

The starting mixture and enzyme solution is heated to between about 120° F. and about 200° F., in particular to between about 140° F. and about 180° F., e.g. 165° F. for about 3 to 5 minutes to initiate gelatinization of starch. The enzyme then reacts on gelatinized starches to break down some of the high molecular weight amylopectin starch fractions (having an average molecular weight of $5.8$-$6.2\times 10^6$ Dalton) into low molecular weight amylopectin starch fractions (having an average molecular weight of $1.7$-$2.0\times 10^6$ Dalton).

The starting mixture and enzyme solution may be mixed in any suitable vessel such as a high speed mixer that permits liquid to be added to free-flowing flour. The output is a free-flowing wetted flour mixture having a moisture content of about 25 to about 40% by weight. The residence time is the time sufficient to obtain the desired result and typically 1 to 5 min.

The enzyme-treated mixture is subsequently added to an extruder (continuous cooker) to gelatinize, hydrolyze, and cook the starch. The mixture resides in the extruder for a time sufficient to gelatinize and cook the starch, but not long enough to dextrinize or otherwise modify the starch to void the whole grain aspect, generally at least 1 minute, typically, about 1 to about 1.5 minutes, to form a dough. Generally, the material is heated from an initial inlet temperature to a final exit temperature in order to provide the energy for starch gelatinization.

Starch gelatinization requires water and heat. The gelatinization temperature range for oats is 127° F. to 160° F. (53-71° C.). If the moisture is less than about 60% then higher temperatures are required.

Heat may be applied through the extruder barrel wall such as with a jacket around the barrel through which a hot medium like steam, water or oil is circulated, or electric heaters imbedded in the barrel. Typically the extrusion occurs at barrel temperatures between 140° F. and 350° F., for example between 175° F. and 340° F., more specifically about 180° F.-300° F.

Heat is also generated within the material by friction as it moves within the extruder by the dissipation of mechanical energy in the extruder, which is equal to the product of the viscosity and the shear rate squared for a Newtonian fluid. Shear is controlled by the design of the extruder screw(s) and the screw speed. Viscosity is a function of starch structure, temperature, moisture content, fat content and shear. The temperature of the dough increases in the extruder to approximately 212° F. and 300° F.

Low shear is applied to the mixture in the extruder. As the enzyme has preconditioned the starch, high shear is not required for this process. High shear makes it difficult to control the degree of hydrolysis. It can also increase the dough temperature excessively, which can overcook it resulting in too much cooked grain flavor. It is noted that the barrel temperature and the dough temperature may be different.

The process balances limiting the dough temperature to avoid too much cooked grain flavor and to keep the enzyme active. The process is balanced such that the dough temperature rises to a sufficient temperature to deactivate the enzyme. Such temperatures are at least 280° F., generally 212° F. to 300° F. A low shear extrusion process is characterized relative to high shear extrusion by high moisture and a low shear screw design versus low moisture and a high shear screw design.

Any suitable extruder may be used including suitable single screw or twin screw extruders. Typical, but not limiting, screw speeds are 200-350 rpm.

The resulting product may be pelletized using a forming extruder and dried, typically to about 1.5 to about 10% by weight, for example 6.5 to 8.5% by weight, moisture content. The pellets may be granulated to a max 5% through a US 40 screen. The particle size of the resulting granulated product is about 10-500 microns, for instance, about 1-450 microns, more particularly about 30-420 microns.

Jet milling may be used to mill the pellets produced in accordance with aspects of the present disclosure. Jet milling creates ultrafine particles. In particular, jet milling reduces the particle size of the pelletized soluble oat flour to less than about 90 micron, for example, less than about 50 microns, such as about 46 microns. As one of ordinary skill in the art would recognize, alternative milling processes can be used to reduce the particle size or micronize the flour to, 0.5-50 microns, such as between 10 to 50 microns.

The resulting soluble oat flour includes beta glucan soluble fiber, such as beta-1, 3-glucan, beta-1, 6-glucan, or beta-1, 4-glucan or mixtures thereof. In addition to beta glucan naturally present in the oats, beta glucan may also be added as approved by the FDA. In certain embodiments, the oat flour preferably contains at least about 3% to 5% or about 3.7% to 4% by weight of beta glucan. In certain embodiments, the oat flour containing liquid, semi-solid, or solid product contains 0.1% to about 1.5% by weight of beta glucan, or about 0.8% to 1.3% by weight of beta glucan. Other amounts of beta glucan are also useful.

The soluble oat flour disperses in less than about 5 seconds in a liquid media at 25° C.

The soluble oat flour prepared in accordance with the process described above may be utilized in a variety of products such as: ready-to-drink (RTD) beverages such as dairy-based beverages and juice-based beverages; powders such as for cold and hot instant beverages, instant pudding, custards, mousses, or gelatin, or as an additive to smoothies or shakes for example; dairy products such as yogurt, ice cream, oat-milk, and processed cheeses such as cream cheese; bakery products such as cookies, muffins, breads, pizza crust, bagels, cakes, crepes, and pancakes; ready-to-eat (RTE) snacks such as pudding, fruit leather, and fruit gel snacks; starters or side dishes such as soups (including, without limitation instant soups and ready-to-eat soups) and congee; seasoning mixes, dressings, and sauces; grain-based foods such as upma and hummus; meat-based foods such as meat balls; polenta; and fillings for food products such as mousse, cream, and fudge. The soluble oat flour may also be used as texture modifiers for bakery products or as a replacement for gums, such as guar gum, for instant oatmeal products. Moreover, the soluble oat flour may be used as a fat replacer in products such as cream-based dips. This list is not all-inclusive and one skilled in the art would recognize that the soluble oat flour may be added to other beverages and food products in accordance with the invention.

It was discovered that the use of the soluble oat flour prepared in accordance with the method described above provides unexpected processing improvements and properties over unprocessed oat flour or soluble oat flour prepared by other methods.

For example, oat flour used in RTE or RTD products is typically pasteurized or sterilized in order to kill microorganisms that could cause disease or spoilage. This high heat process ensures that the flour is safe and healthy to consume. Such pasteurization and sterilization cannot be easily done on dry flour. Hence, prior to pasteurization or sterilization, the oat flour needs to be completely hydrated to ensure appropriate heat transfer through the oat flour during the kill step. Full hydration and complete gelatinization of the oat flour are desired to ensure the viscosity of the product will not dramatically increase during further processing.

Oat flour is typically hydrated by dispersing the oat flour in water and heating the slurry using an appropriate time and temperature combination that results in starch gelatinization. Typically the temperature is 90° C. and the time to hydrate fully is at least 25 minutes. Lower hydration temperatures will require longer times. Then the slurry needs to be cooled down to blend the other ingredients. Then the oat flour slurry may be pasteurized or sterilized by any suitable means such as High Temperature Short time (HTST) pasteurization or Ultra High Temperature (UHT) sterilization. Pasteurization or sterilization is a necessary step for RID or RTE liquid or semi-solid foods.

It was discovered that soluble oat flour made in accordance with the process described above hydrates without the need of a lengthy heating process of standard or typical oat flour. The quality of the oats is maintained, that is the integrity of the oat flour is maintained throughout the process. With soluble oat flour, the temperature may be around chilled to room temperature, typically 4 to 30° C. reducing the total processing time by 1.5 hours. Typically the amount of soluble oat flour in the water is 2% to 10% by weight, or 3% to 9% by weight, or 4% to 8% by weight. Then the flour may be further processed to prepare the RTE or RTD product.

Furthermore, it was discovered that after hydration, the soluble oat flour slurry has a much lower viscosity compared to standard or typical oat flour slurry. The standard oat flour produced a much higher viscosity than soluble oat flour especially at higher concentrations of oats. In fact, the viscosity of the soluble oat flour slurry at 8% by weight oats is lower than the viscosity of oat flour at 4% by weight oat concentration.

Such improved viscosity and hydration results were not expected and has thus allowed the soluble oat flour to be used in products to provide better properties such as better hydration and mixing properties, particularly without the need of elevated temperatures. The viscosity of hydrated soluble oat flour in water in amounts of 2% to 10% by weight will generally ranges from 100 to 1600 cP at 24° C.

For typical oat flours, high shear mixing must be used with the hydrated flour prior to adding to beverage ingredients, to reduce viscosity. Because of the relatively low viscosity of the soluble oat flour, there is no need for such a high shear mechanical process step to reduce viscosity driven by starch. Gentle mixing is sufficient.

Therefore, benefits of using soluble oat flour for beverages instead of typical oat flour include simplified manufacturing processes and less capital investment for heating, mixing and cooling equipment.

Soluble oat flour is very effective in dairy beverages because no high temperature heating is required. As discussed above, typically high temperature and time is involved in oat flour hydration. If one wants to use typical oat flour in a dairy beverage, it is recommended to hydrate the oat flour in water because heating fluid milk to the high temperatures required for hydration results in cooked milk flavors. To be able to produce a beverage with high concentration of dairy components, the dairy components must be added as a dairy powder. In contrast, soluble oat flour allows hydration to occur directly in the fluid milk, producing a product with better sensorial properties, for instance, a fresher flavor is associated with the product since the cold milk has not been subjected to a severe heat hydration treatment and therefore does not have the cooked notes commonly associated with heat treating milk. Attention is drawn to U.S. Ser. No. 13/547,733 which is hereby incorporated by reference in its entirety, which describes the benefits of hydrolyzed oat flour in dairy beverages.

Soluble oat flour may also be used in juice beverages. Soluble oat flour can be hydrated in the juice at ambient temperatures or cold temperatures. The juice may be any suitable juice or juice/puree combination. Suitable juices may be acidic or non-acidic, fruit, vegetable, or combinations thereof. Non-limiting examples of juices and purees include, Acai, Aloe Vera Juice, Apple Apricot Nectar, Bancha, Beet, Black Cherry, Black Currant, Blackberry, Blueberry, Boysenberry, Carrot, Celery Coconut, Cranberry, Cucumber, Elderberry, Gogi Berry, Grape, Grapefruit, Kiwi, Strawberry, Tomato, Raspberry, Lemon, Lime, Mango, Orange, Papaya Nectar, Passion fruit, Pear, Pineapple, Plum, Pomegranate, Potato, Prune, Pummelo, Radish, Razzleberry, Sorrel, Spinach, Tangerine, Tomato, Turnip, Watercress, Watermelon, and Wheat Grass. Purees are well-known to those skilled in the art and are generally prepared from smashed or mashed fruits and vegetables.

The following embodiments are also contemplated.

Clause 1. A method of reducing systemic chronic inflammation (SCI) in a subject comprising: administering an effective amount of a composition to provide about 2 g to about 5 g of beta-glucan and about 1 mg to about 2 mg of avenanthramides to the subject, wherein the subject has a biological age of about 45 to about 115, and wherein the subject has an LDL cholesterol level of at least 3 mmol/L.

Clause 2. The method of clause 1, wherein the composition is provided in a form for oral consumption by the subject.

Clause 3. The method of clause 1 and 2, wherein the form is a capsule, beverage, foodstuff, or a powder capable of being added to a beverage or foodstuff.

Clause 4. The method of clauses 1 to 3, wherein the composition is administered once, twice, three, four, or five times per day to the subject resulting in a total administration of at least about 2 g of beta-glucan and at least about 1 mg of avenanthramides to the subject.

Clause 5. The method of clauses 1-4, wherein the composition comprises at least about 50% hydrolyzed starch molecules of a total starch content, and wherein the hydrolyzed starch molecules have an average molecular weight of no more than $3.4 \times 10^6$ Dalton.

Clause 6. The method of clause 5, wherein the composition is formed from oat bran.

Clause 7. The method of clauses 1 to 6, wherein the composition contains at least 0.75 g of beta-glucan.

Clause 8. The method of clauses 1 to 7, wherein the composition is administered in a dosing regimen that occurs for at least two weeks, at least three weeks, or at least four weeks.

Clause 9. The method of clauses 1 to 8, wherein the biological age is reduced by at least two years.

Clause 10. The method of clauses 1 to 9, wherein the SCI may be diagnosed based on the expression levels of certain biomarkers.

Clause 11. The method of clause 10, wherein the biomarkers are selected from Eotaxin-1 (i.e., CCL11), IFNγ, Gro-α, MIG, TRAIL, or a combination thereof.

Clause 12. A method of reducing systemic chronic inflammation (SCI) in a subject comprising: administering an effective amount of a composition to provide about 2 g to about 5 g of beta-glucan and about 1 mg to about 2 mg of avenanthramides to the subject, wherein the subject has a biological age of about 45 to about 115, wherein the subject has an LDL cholesterol level of at least 3 mmol/L, and wherein the reduction in SCI may be measured by showing a reduction in the expression level of biomarkers in the subject after administering the composition compared to an expression level of biomarkers before administering the composition.

Clause 13. The method of clause 12, wherein one or more of the biomarkers are selected from Eotaxin-1 (i.e., CCL11), IFNγ, Gro-α, MIG, or TRAIL.

Clause 14. The method of clauses 12 to 13, wherein the composition is provided in a form for oral consumption by the subject.

Clause 15. The method of clauses 12 to 14, wherein the composition is provided as a capsule, beverage, foodstuff, or a powder capable of being added to a beverage or foodstuff.

Clause 16. The method of clauses 12 to 15, wherein the composition is administered once, twice, three, four, or five times per day to the subject resulting in a total administration of at least about 2 g of beta-glucan and at least about 1 mg of avenanthramides to the subject.

Clause 17. The method of clauses 12 to 16, wherein the composition comprises at least about 50% hydrolyzed starch molecules of a total starch content, and wherein the hydrolyzed starch molecules have an average molecular weight of no more than $3.4 \times 10^6$ Dalton.

Clause 18. The method of clauses 12 to 17, wherein the composition is formed from oat bran.

Clause 19. The method of clauses 12 to 18, wherein the composition contains at least 0.75 g of beta-glucan.

Clause 20. The method of clauses 12 to 19, wherein the composition is administered in a dosing regimen that occurs for at least two weeks, at least three weeks, or at least four weeks.

Clause 21. The method of clauses 12 to 20, wherein the biological age of the subject is reduced by at least two years.

EXAMPLES AND METHODOLOGY

In a double-blinded placebo-controlled study, the effect of a soluble oat bran concentrate (SoluOBC, PepsiCo Inc.) was investigated on systemic chronic inflammation biomarkers. More information about the process to produce SoluOBC is provided in U.S. Patent Publication Serial No. 2017/0273337, published Sep. 28, 2017, now U.S. Pat. No. 11,172,695 issued Nov. 16, 2021; and U.S. Pat. No. 9,510,614 issued Dec. 6, 2016, the contents of which are hereby incorporated in their entirety. Briefly, SoluOBC includes oats that have been processed to partially hydrolyze the starch, the fiber, or both. Serum samples from an interventional study of blood lipid cardiovascular biomarkers where individuals were supplemented with 3 g/day of SoluOBC (treated) or placebo (untreated) were collected at three time points (baseline 0, week 2, and week 4). The Inflammatory Age (iAge®) test (Edifice Health Inc.) was utilized to analyze the biomarkers. Additional information about the Inflammatory Age test is provided in U.S. Patent Application Publication 2021/0109109 published Apr. 15, 2021, the entire contents of which are incorporated herein. Individuals with elevated baseline iAge® and LDL cholesterol exhibited a benefit from the treatment.

Example 1: Study Cohort and Treatment

A double-blinded placebo-controlled interventional study was conducted in 191 healthy male and female patients (38% male, 62% female) ranging from 21 to 65 years of chronological age (the average age was 48) with moderate to elevated LDL-cholesterol levels. The study was conducted over four weeks with blood sampling every two weeks by standard venipuncture. The SoluOBC treatment group was given in 20 g sachets providing one-gram of β-Glucan to be taken three times a day (N=96 subjects in treatment group). The placebo group (untreated) was given rice powder to match weight, energy (kcal), total fats, saturated fats, total carbohydrates, available carbohydrates, and protein concentration to the treatment and taken at the same frequency (N=95 subjects). Table 1 provides the components of each sachet. Serum samples (N=573) were obtained from individuals at baseline, week 2 and week 4. Blood levels of Hemoglobin (g/L), Urea (mmol/L), Creatinine (μmol/L), GGT (U/L), ALT (U/L), AST (U/L), % SFA, triglycerides (mmol/L), HDL (mmol/L), LDL (mmol/L), cholesterol (mmol/L), fasting glucose (mmol/L), glycated albumin (mmol/L), insulin (mIU/L) were analyzed at baseline, two weeks and four weeks. At each visit, blood pressure, heart rate and weight were measured, and several subjective questions were answered by each subject. Serum samples were analyzed using Inflammatory Age modifiers and iAge® determination.

TABLE 1

Components of compositions

|  | SoluOBC (treatment) | Rice Powder (placebo) |
| --- | --- | --- |
| Weight (g) | 23 | 22 |
| Energy (kcal) | 83 | 81 |
| Total fat (g) | 1 | 1 |
| Saturated fat (g) | 0 | 0 |
| Total carbohydrates (g) | 17 | 18 |
| Available carbohydrates (g) | 14 | 16 |
| Total fiber (g) | 2 | 0.3 |
| Beta-Glucan (g) | 1 | 0 |
| Avenanthramides (mg) | 0.38 | 0 |
| Total Phenolics (mg) | 15.6 | 11.4 |
| GABA (mg) | 0.607 | 0.368 |
| Protein (g) | 2 | 2 |

Example 2: iAge® (Biological Age) Determination

Samples were analyzed using a Luminex LX-200 instrument to determine the levels of iAge® markers composed of 5 core proteins CCL11 (aka Eotaxin-1), IFN-γ, GRO-α, CXCL9 and TRAIL. Normalized mean fluorescence intensity (MFI) values for each plate were prepared by setting values below the 5th percentile to the 5th percentile of the plate and those values above the 95th percentile were set to the 95th percentile of the plate. These values were normalized using control serum samples from eleven individuals, both male and female, spanning the chronological ages of 23-83 years old. iAge® was derived for all study participants using the machine learning algorithms as discussed above using the normalized MFI values. The systemic chronic inflammation (SCI) index was calculated for each individual from the empirical cumulative distribution of iAge® in the study population from the same decade as the individual.

Example 3: Statistical Analysis

Samples were grouped by treatment. Change in the inflammatory biomarkers or iAge® at week two from baseline and at week four from week two were compared using a one-tailed pairwise t-test. The least absolute shrinkage and selection operator (LASSO) machine learning algorithm was implemented using the elastic net module in R and used to train a model on age, sex, ethnicity, and other measured baseline traits to predict responders to treatment in the treated group and untreated group. The predictive power of the known and measured attributes in this model is derived from the variable coefficients of the LASSO analysis. A responder has a decrease in iAge® from baseline to week two. The variable with the largest coefficient in the LASSO model (baseline iAge®) was used to calculate the optimal cut point that individuals are responders to the treatment using cutpointR. Responders were identified within the treatment group as the difference in iAge® at week two from baseline starting at zero and decreasing by one until the area under the curve no longer increased. Similarly, those with high iAge® at baseline were used to calculate the optimal cut point for LDL-cholesterol level at baseline, which was used to identify additional responders to the treatment.

Example 4: SoluOBC Treatment Trends with a Reduction in iAge® and CCL11

Figure 1C:
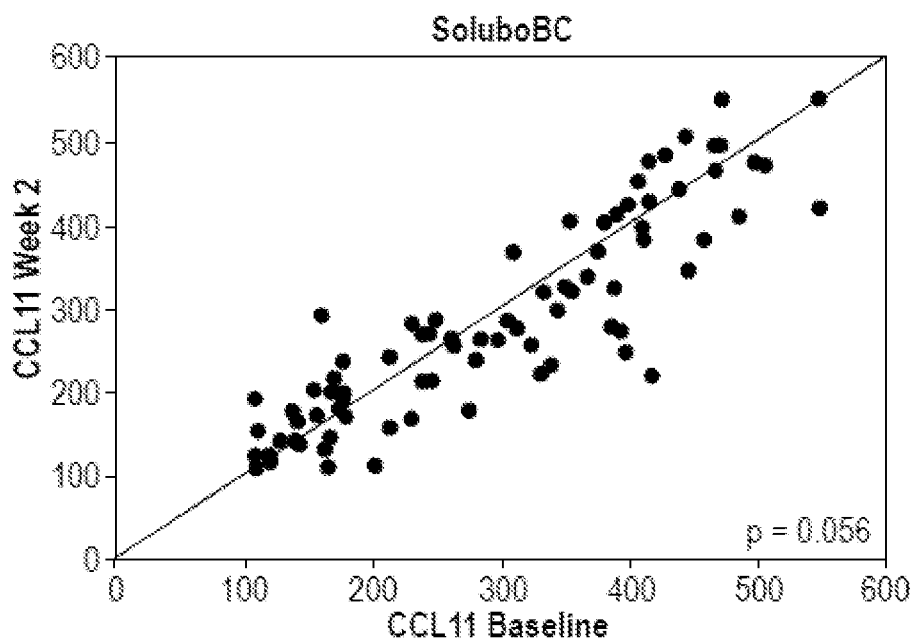
FIG. 1C is a graph comparing the CCL11 levels at baseline to the week two CCL11 levels for the treated group.
Figure 1D:
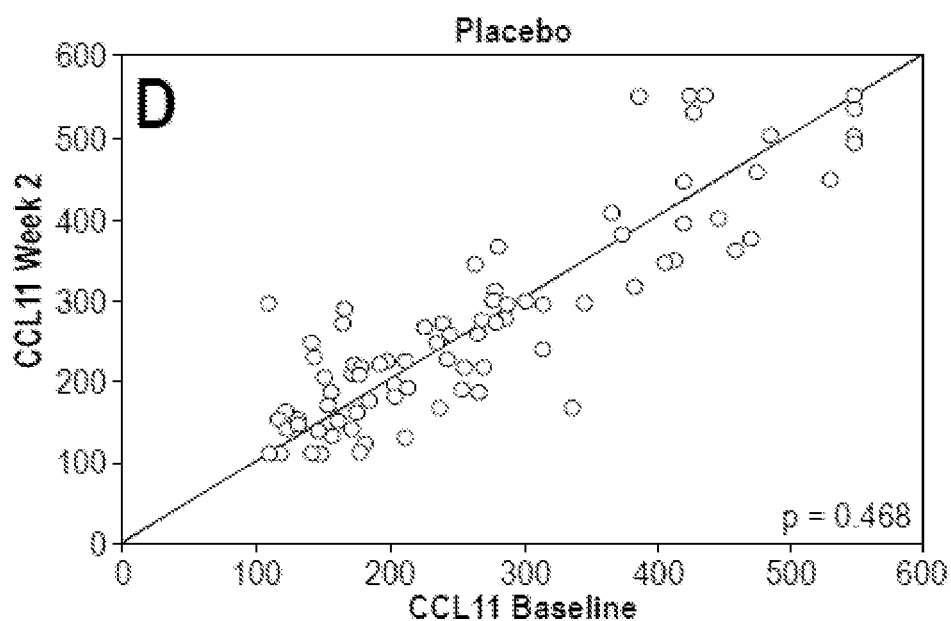
FIG. 1D is a graph comparing the CCL11 levels at baseline to the week two CCL11 levels for the untreated group.
Figure 6A:
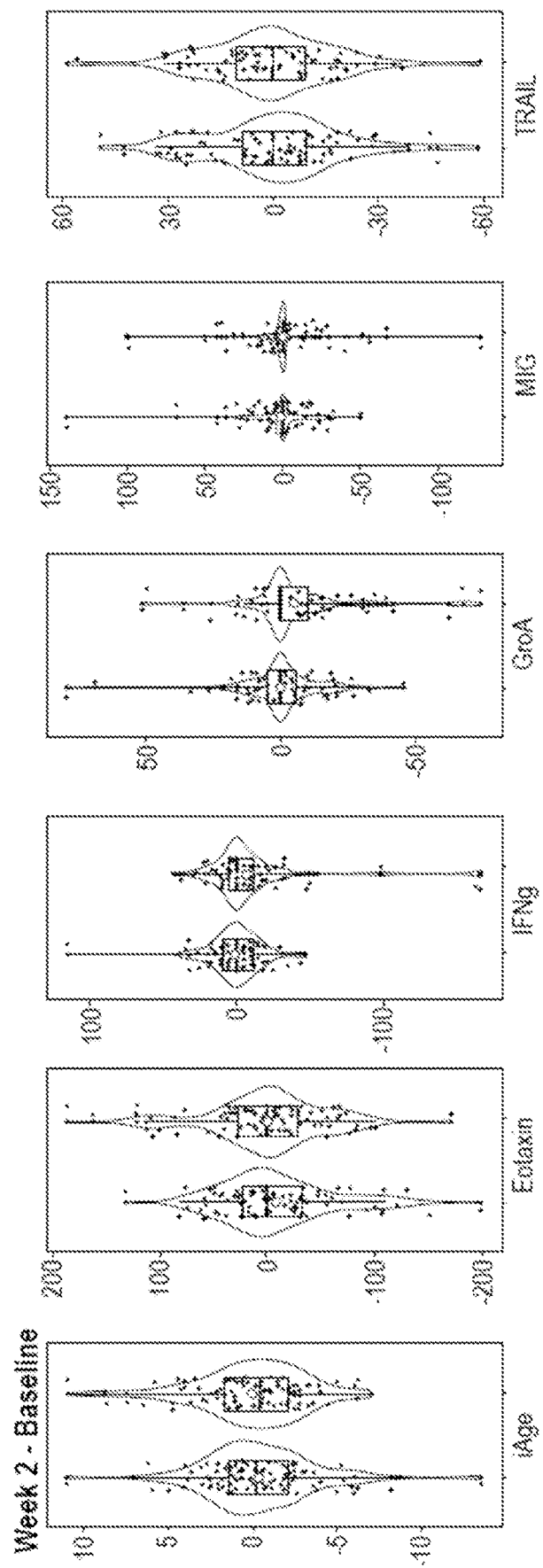
FIG. 6A shows the change between the baseline and week 2 values for iAge and each analyte (Eotaxin-1 (CCL11), IFNγ, Gro-α, MIG, and TRAIL) for the treatment (blue) and non-treatment (green) treated groups.
Figure 6B:
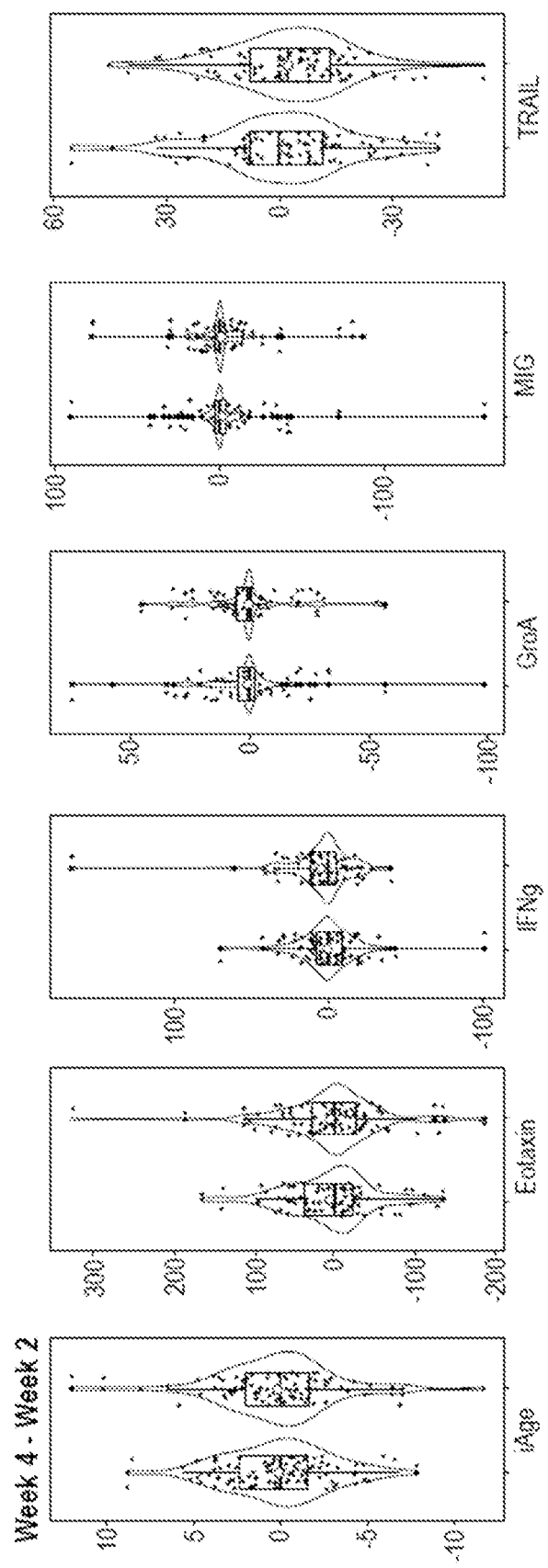
FIG. 6B shows The change between the week 2 and week 4 values are shown for iAge and each analyte (Eotaxin-1 (CCL11), IFNγ, Gro-α, MIG, and TRAIL) for the treatment (blue) and non-treatment (green) treated groups.

A total of 573 serum samples were interrogated from each study participant (N=191) across 3 time points (baseline, week two, and week four) using the iAge® technology. Analysis of blood iAge® at baseline vs. week two revealed a trend towards a decrease in iAge® in the treated group (−0.37 iAge® years, P=0.136) but not in the untreated group (+0.04 iAge® years, P=0.453) (FIGS. 1A and B). The levels of circulating CCL11 substantially decreased at week two compared to baseline in the treated group (3% change, P=0.056) and remained unchanged in the untreated group (0.2%, P=0.468) (FIGS. 1C and 1D). Of those analyzed, no additional iAge® proteins were significantly affected by the SoluOBC intervention (FIG. 6A). No significant changes were observed in iAge® levels between week four and week two in the SoluOBC group (FIG. 6B). IFN-γ decreased significantly in untreated group at weeks two and four relative to baseline (P=0.012 and 0.029), and Gro-α likewise decreased significantly at week two relative to baseline (P=0.042) (FIGS. 6A and 6B). These changes in inflammatory biomarkers for the placebo (untreated) group had no effect on iAge® levels in this group (Data not shown).

Together, these results indicate that SoluOBC can modulate age-related iAge® proteins (such as CCL11) in humans. The group that received SoluOBC treatment trended towards decreased iAge® (P=0.13) over a two-week period versus the control group (not significant), and the SoluOBC treated group significantly decreased CCL11 levels (P=0.06) over a two-week period versus the control group (not significant).

Example 5: Baseline iAge® Predicts Effectiveness of SoluOBC Treatment

Figure 2A:
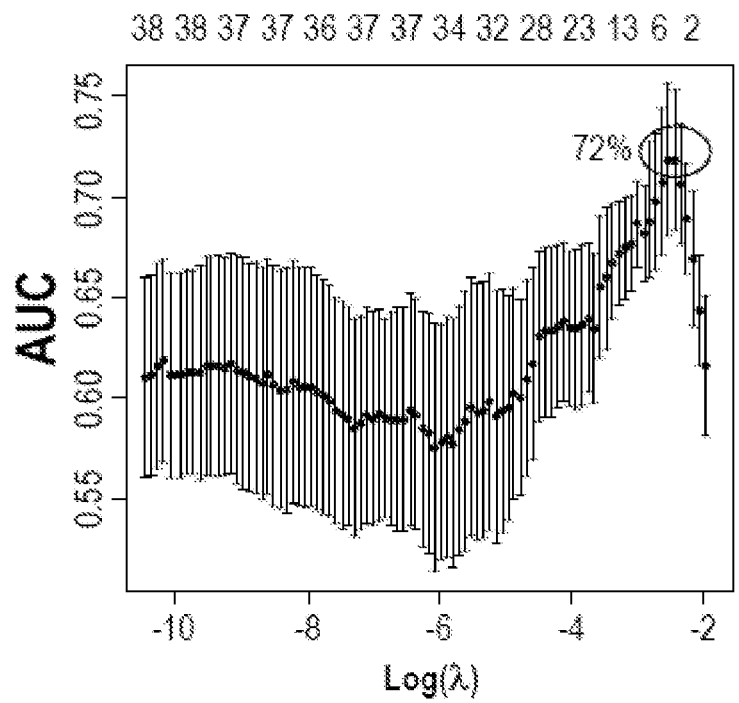
FIG. 2A is a graph showing four variables are useful predictors to identify responders and non-responders within the treated group.
Figure 2B:
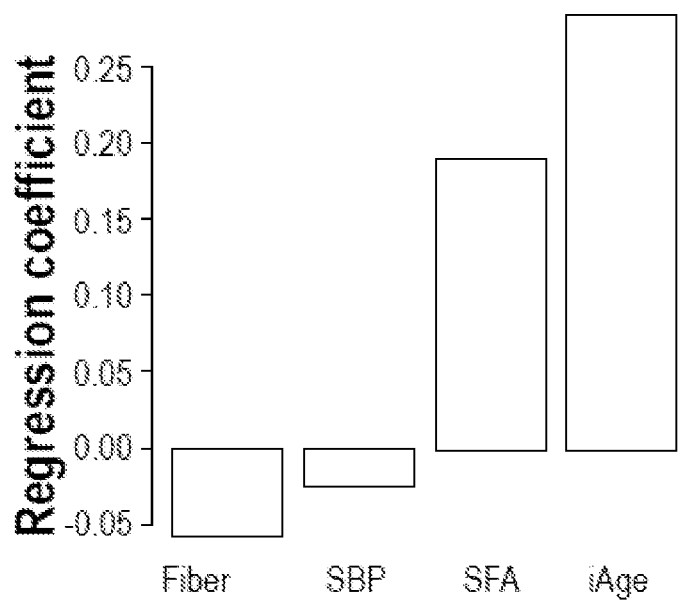
FIG. 2B is a graph showing that of the four variables, two are negative predictors and two are positive predictors.

The trend observed in the reduction of iAge® in the treated group can be used to classify predicted responders and predicted non-responders to the treatment. The Least Absolute Shrinkage and Selection Operator (LASSO) regression was employed, a standard machine learning approach largely utilized for predictive tasks and feature selection. The LASSO regression imposes a penalty to the regression coefficients, such that small coefficients are shrunk to zero and only the most relevant features are selected. The changes in iAge for each subject in the study were calculated and a total of 39 baseline features including subject's demographics, blood biomarkers for cardiovascular health and lipid fractions, liver function, metabolism and inflammation were used as input (predictor) variables (see Example 3). Using this method, four variables were selected for the prediction of the changes in iAge® in week two versus baseline and these provided a relatively good prediction (cross-validated AUC, cvAUC=0.72) (See FIG. 2A). Of the four baseline predictors selected by the model (FIG. 2B), two were negative predictors and these include total fiber content (g/d) and systolic blood pressure and two were positive including the percentage of dietary saturated fatty acid intake (% SFA) and baseline iAge, which was the strongest predictor of response to the SoluOBC intervention (FIG. 2B). The model for the prediction of changes in iAge® using baseline parameters in the untreated group yielded a cvAUC=0.48 (no different than random), suggesting that no relevant features contribute to classification of responders vs. non responders in the untreated group (FIG. 2C).

Figure 3C:
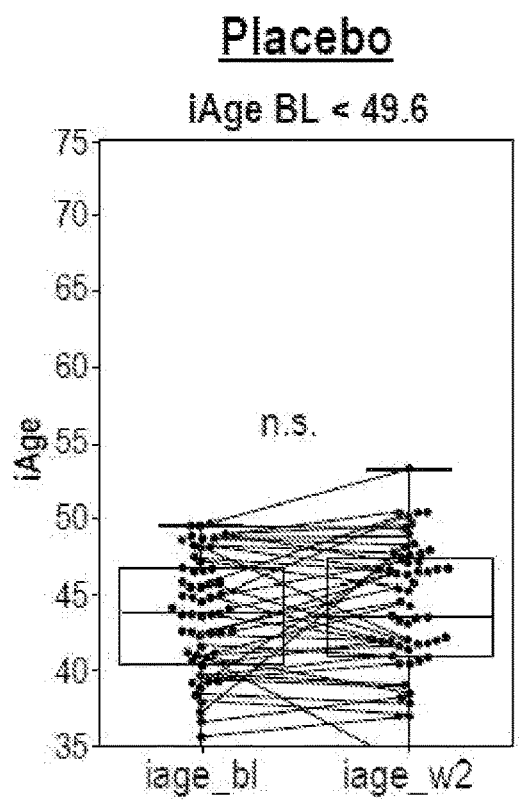
FIG. 3C is a graph comparing the iAge® at baseline to week two for the untreated group having an initial baseline iAge® score less than 49.6
Figure 3D:
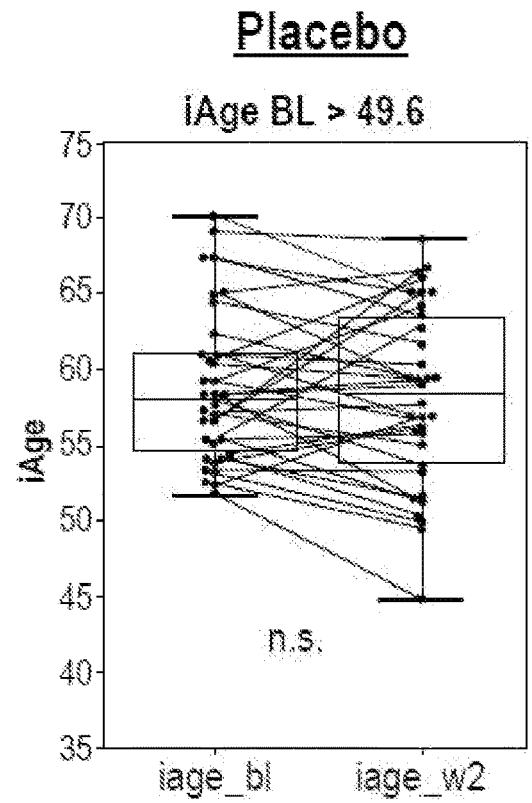
FIG. 3D is a graph comparing of iAge® at baseline to week two for the untreated group having an initial baseline iAge® score greater than 49.6.
Figure 3E:
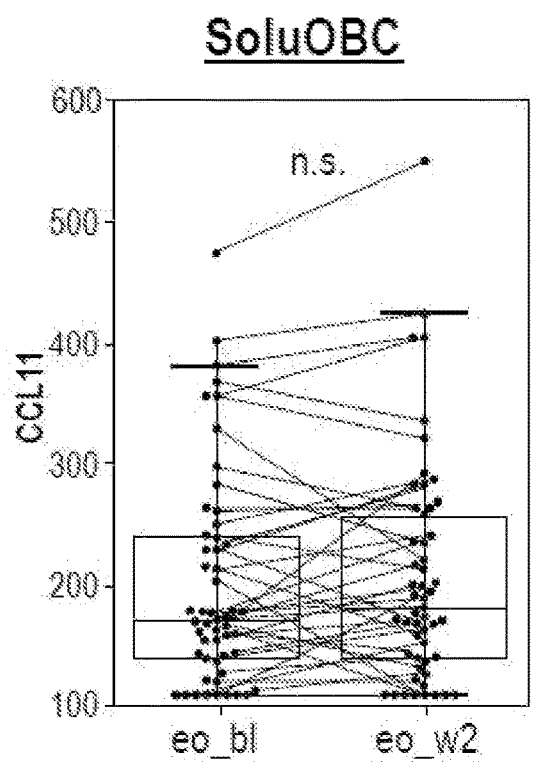
FIG. 3E is a graph comparing the CCL11 level at baseline to week two for the treated group having an initial baseline iAge® score is less than 49.6.
Figure 3F:
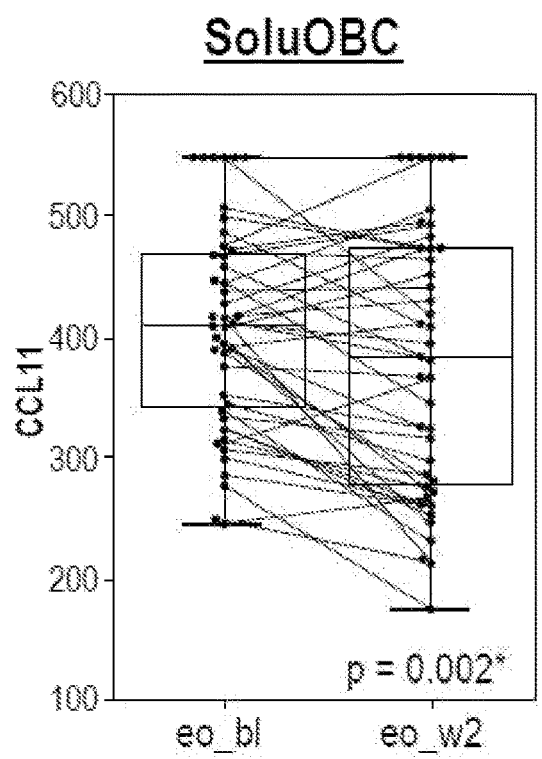
FIG. 3F is a graph comparing the CCL11 level at baseline to week two for the treated group having an initial baseline iAge® score is greater than 49.6.

Example 6: High Baseline iAge® and LDL Levels Correlate with Decreased iAge® and CCL11 in Response to SoluOBC Elevated iAge® and circulating LDL have been shown to independently contribute to accelerated cardiovascular pathology. To explore whether iAge and LDL could further subset subjects who exhibit maximum benefit from SoluOBC, a baseline iAge® was identified and used to apply an unbiased approach to divide the 191 participants into those with low and high baseline iAge® with change in iAge® at week two as the output variable. To do so, cutpointR, a standard method largely utilized in diagnostic testing that automatically selects optimal cutpoints for a given outcome variable (see Example 3) was used. The optimal separation of responders and non-responders to SoluOBC was observed at an iAge® value of 49.6 years. Individuals with an iAge® above or below 49.6 were classified as "high" and "low" iAge® groups, respectively. Within the treated group, the high iAge® group exhibited a significant decrease in iAge® at week two (−1.46 iAge years, P=0.008) whereas no significant change was observed in the low iAge® group (FIGS. 3A and 3B). No significant change in iAge® was observed in the low or high iAge® groups of the untreated group (FIGS. 3C and 3D). Similarly, the high iAge® group in the treated group showed a significant decrease in CCL11 at week two (−6.9% change, P=0.002) but no significant decrease was observed in the low iAge® treated group (FIGS. 3E and 3F). No significant change in CCL11 was observed in either the "low" or the "high" iAge® groups within the untreated group (FIGS. 3G and 3H).

Figure 4:
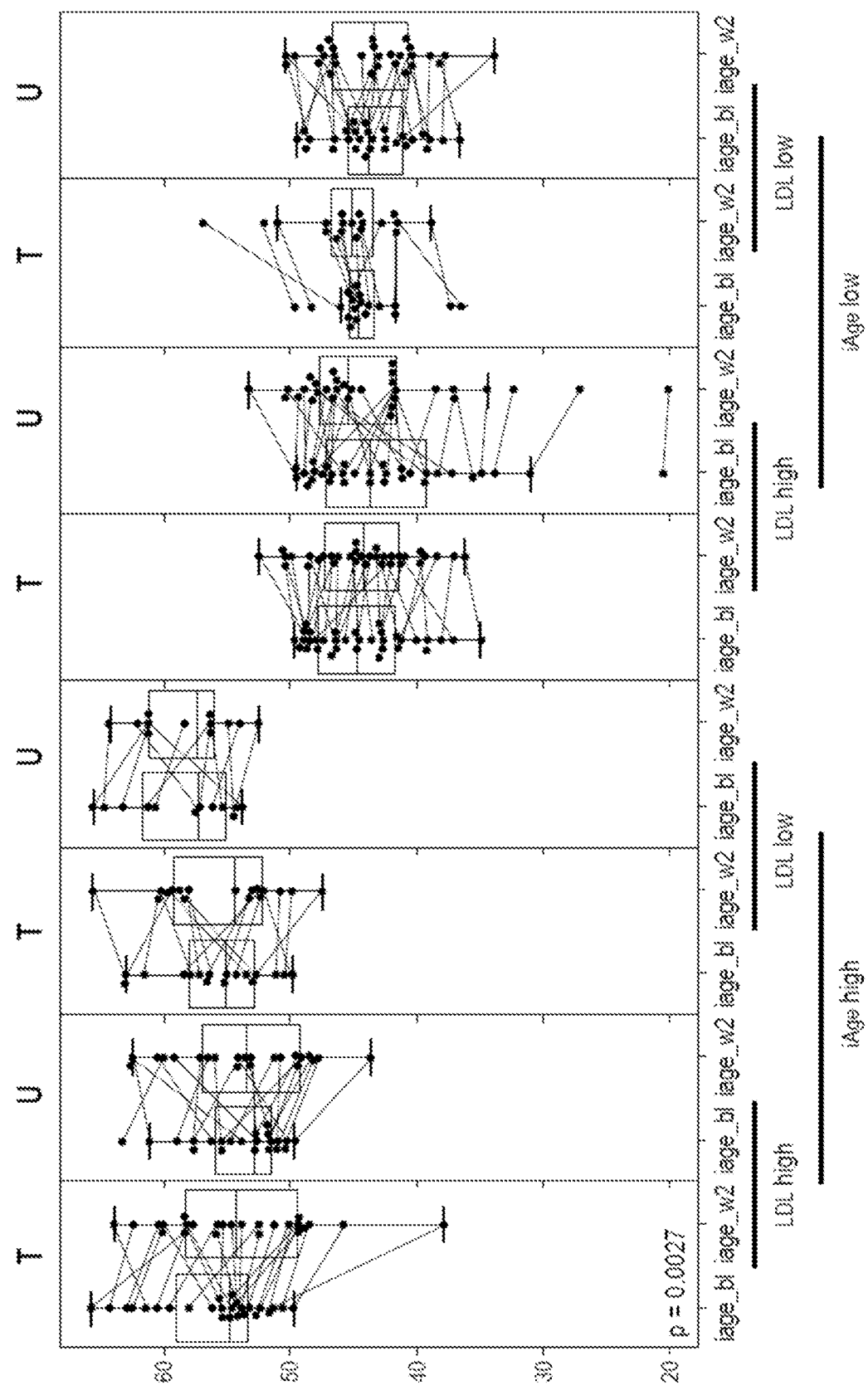
FIG. 4 is a graph showing the treated (T) and untreated (U) groups subdivided into high/low baseline iAge® using a cut-off of 49.6 years and high/low baseline LDL levels using a cut-off of 3.27 mmol/L.

Next, to examine the effect of baseline LDL on further subject classification within the responder (high baseline iAge®) and non-responder (low baseline iAge®) groups, the cutpointR method was employed, as before, with circulating baseline LDL levels as the input variable. The most powerful cutoff for baseline LDL levels was 3.27 mmol/L to predict response in patients with high baseline iAge®. For individuals with high baseline iAge® and LDL levels, there is a significant decrease in iAge® between baseline and week two for the SoluOBC treated group (−2.3 yr, p=0.0027) compared to untreated group (p=0.27) (FIG. 4). No other combination of baseline iAge® and LDL levels provided a significant decrease in iAge® between baseline and week two. Unexpectedly, SoluOBC treated subjects with low baseline iAge® and low LDL showed an increase in iAge® between baseline and week two (+1.6 yr, p=0.018). These results suggest that treatment positively impacts iAge® in individuals with elevated baseline iAge® years.

Example 7: Changes in iAge® Induced by SoluOBC are Mediated by a Decrease in CCL11

Figure 5A:
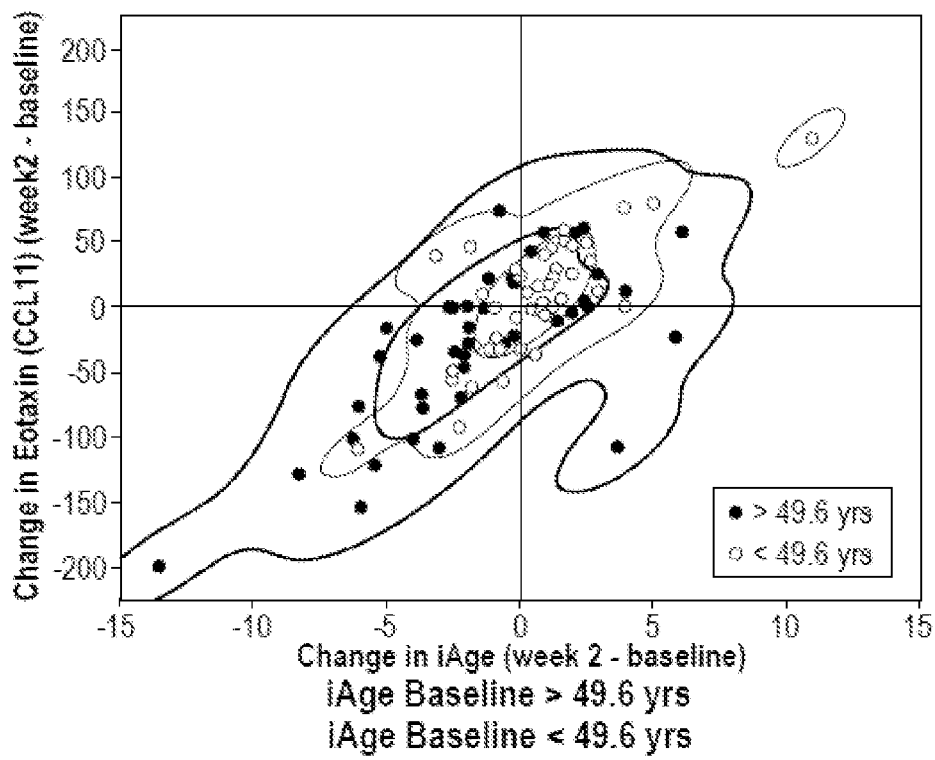
FIG. 5A shows a change in iAge® compared to the change in CCL11 for the treated group for individuals with high (blue) or low (grey) baseline iAge®.
Figure 5B:
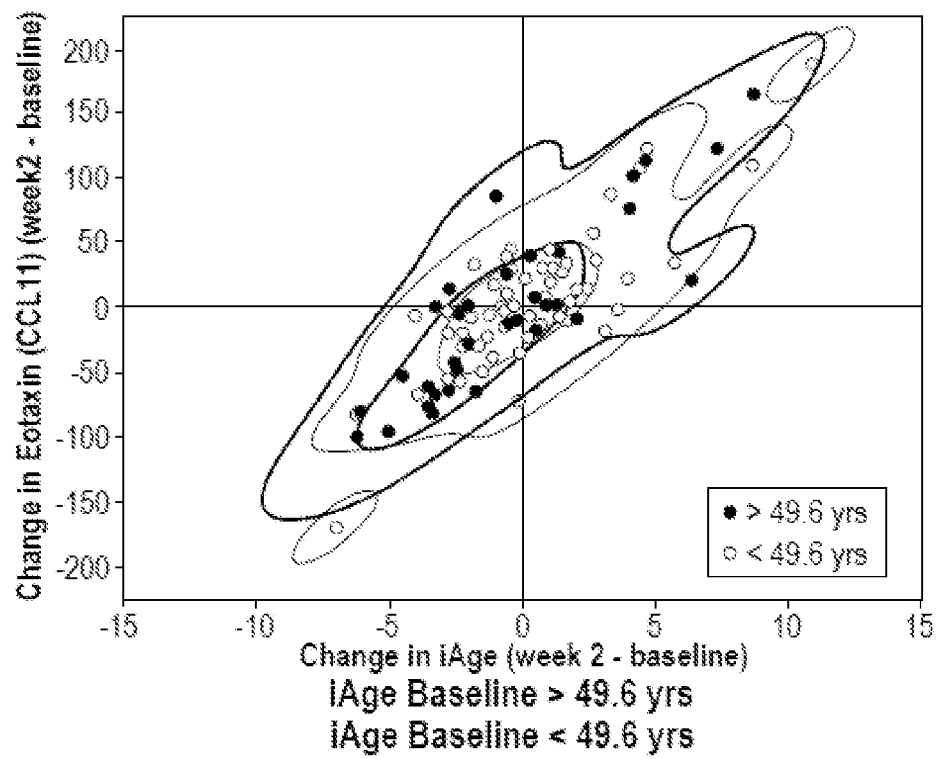
FIG. 5B shows a change in iAge® compared to the change in CCL11 for the untreated group for individuals with high (red) or low (grey) baseline iAge®.

To investigate which inflammation biomarkers (proteins) were targets for SoluOBC treatment and may drive the modifications in the observed iAge®, the changes in iAge® induced by SoluOBC treatment at week two were compared with expression level changes observed in the biomarker proteins. In subjects with baseline high iAge® (>49.6 iAge® years), decreasing circulating levels of CCL11 tracked with changes at week two observed in iAge® following SoluOBC treatment (FIG. 5A). No significant decreases in both CCL11 and iAge® were observed in subjects with low iAge® (<49.6 iAge® years) in the treatment group (FIG. 5A). Similarly, no changes were detected in either the low or the high iAge® groups in the untreated group (FIG. 5B). Together, these results indicate the improvements in iAge® observed in the SoluOBC group are due to the components of the treatment, which may directly or indirectly target CCL11 and modify its expression.

It will be understood that the invention has been described above purely by way of example, and modifications of detail can be made within the scope of the invention.

Each feature disclosed in the description, and (where appropriate) the claims and drawings may be provided independently or in any appropriate combination.

While the concepts of the present disclosure are susceptible to various modifications and alternative forms, specific exemplary embodiments of the disclosure have been described by way of example in the detailed description. It should be understood, however, that there is no intent to limit the concepts of the present disclosure to the particular disclosed components and methods; the intention is to cover all modifications, equivalents, and alternatives falling within the spirit and scope of the invention as defined by the claims.

The invention claimed is:

1. A method of lowering low density lipoprotein cholesterol in a human in need thereof consisting essentially of administering to the human in need thereof a composition that consists essentially of (i) about 1 mg to about 2 mg of avenanthramides and (ii) a soluble oat flour produced by hydrolyzing oat flour, maltodextrin, sugar, and mixed tocopherols with an alpha amylase, wherein the soluble oat flour contains hydrolyzed starch molecules with an average molecular weight of no more than $3.4 \times 10^6$ Dalton and from about 2 g to about 5 g of beta-glucan, wherein the composition is administered to the human in need thereof to effectively lower the low density lipoprotein cholesterol in the human.

* * * * *